United States Patent [19]

Namen et al.

[11] Patent Number: 5,328,988
[45] Date of Patent: Jul. 12, 1994

[54] INTERLEUKIN-7

[75] Inventors: Anthony E. Namen; Raymond G. Goodwin; Stephen D. Lupton; Diane Y. Mochizuki, all of Seattle, Wash.

[73] Assignee: Immunex Corporation, Seattle, Wash.

[21] Appl. No.: 957,649

[22] Filed: Oct. 6, 1992

Related U.S. Application Data

[60] Continuation of Ser. No. 511,438, Apr. 13, 1990, abandoned, which is a division of Ser. No. 255,209, Oct. 7, 1989, Pat. No. 4,965,195, and a continuation-in-part of Ser. No. 113,566, Oct. 26, 1987, abandoned.

[51] Int. Cl.$^5$ .................. C07K 13/00; A61K 37/02
[52] U.S. Cl. .................................. 530/351; 424/85.2; 930/141; 435/69.52
[58] Field of Search ................... 530/351; 424/85.2; 930/141; 435/69.52

[56] References Cited

U.S. PATENT DOCUMENTS

| | | |
|---|---|---|
| 4,425,437 | 7/1982 | Riggs . |
| 4,518,584 | 12/1983 | Mark et al. . |
| 4,530,901 | 2/1980 | Weissmann . |
| 4,703,008 | 11/1984 | Lin . |
| 4,720,482 | 1/1988 | Cantor et al. ............... 514/2 |
| 4,730,036 | 3/1988 | Ralph et al. ............... 530/412 |
| 4,956,281 | 6/1987 | Wallner et al. . |
| 4,965,195 | 10/1988 | Namen et al. . |
| 4,968,607 | 2/1988 | Dower et al. . |
| 5,032,676 | 10/1986 | Deeley et al. . |
| 5,037,756 | 4/1986 | Bollum et al. . |
| 5,071,972 | 10/1988 | Larsen . |
| 5,081,019 | 5/1990 | Wallner et al. . |
| 5,116,738 | 4/1991 | Wang et al. . |
| 5,128,450 | 6/1989 | Urdal et al. . |
| 5,134,121 | 1/1991 | Mobley et al. . |
| 5,141,856 | 12/1989 | Collins et al. . |

FOREIGN PATENT DOCUMENTS

| | | |
|---|---|---|
| 0212914 | 3/1987 | European Pat. Off. . |
| 8805469 | 7/1988 | PCT Int'l Appl. . |

OTHER PUBLICATIONS

Oliver and Ward, A Dictionary of Genetic Engineering, p. 49, Cambridge University Press, Cambridge (1985).
Cerretti et al, PNAS 83, 1986 pp. 3223-3227.
Fung et al, Nature 307, 1984, pp. 233-237.
Fung et al. "Molecular cloning of cDNA for murine interleukin-3" Nature 307: 233-237 (1984).
Cerretti et al. "Cloning, sequence, and expression of bovine interleukin 2" Proc. Natl. Acad. Sci. USA 83: 3223-3227 (1986).
Maniatis et al. (1982) in Molecular Cloning: A Laboratory Manual (Cold Spring Harbor Laboratory, Cold Spring Harbor, N.Y.). (pp. 224-246 and 404-433).
Paige, C. S. "Surface immunoglobulin-negative B-cell precursors detected by formation of antibody-secreting colonies in agar." Nature 302:711, 1983.
Paige, C. S. et al. "Differentiation of murine B cell precursors in agar culture. Frequency, surface marker analysis and requirements for growth." Eur. J. Immunol. 14:979-987, 1984.
Giri, J. G. et al. "Interleukin-1-mediated induction of K-light chain synthesis and surface immunoglobulin expression on pre-B cells." J. Immunol. 132-233, 1984.
Jyonouchi, H. et al., "Humoral factors in very young NZB mice that enhance the maturation of normal B cell precursors. Partial purification and characterization." J. Immunol. 135:1891, 1985.
Landreth, K. S. et al. "Regulation of human B lymphopoiesis: Effect of a urinary activity associated with cyclic neutropenia." J. Immunol. 134:2305, 1985.
Whitlock, C. A. et al. "Murine B cell lymphopoiesis in long term culture." J. Immunol. Meth. 67:353, 1984.
Whitlock, C. A. et al. "Bone marrow stromal cell lines with lymphopoietic activity express high levels of a pre-B neoplasia-associated molecule." Cell 48:1009-1021 (1987).
Hunt, P. et al. "A single bone marrow-derived stromal cell type supports the in vitro growth of early lymphoid and myeloid cells." Cell 48:997-1007 (1987).
Namen, A. E. et al. "B cell precursor growth-promoting activity." J. Exp. Med. 167:1002, 1988.
Namen, A. E. et al., "Stimulation of B-cell progenitors by cloned murine interleukin-7." Nature 333:571-573 (1988).

Primary Examiner—Garnette D. Draper

[57] ABSTRACT

Mammalian Interleukin-7 proteins (IL-7s), DNAs and expression vectors encoding mammalian IL-7s, and processes for producing mammalian IL-7s as products of cell culture, including recombinant systems, are disclosed.

4 Claims, 8 Drawing Sheets

FIGURE 2:

```
   1 CTTGCAATAG CGAGCTTTCT CTGCTGCACA TTTGTGGCTT CTGTGGACAT
  51 ATTAGTAACC AGCGGTTTTA GCTCCCAGTC TCACAGAGTT GCCAGAGAGG
 101 TTAGAAGTCA TTTGAAAAGC CTATTAGCCG AATCTTTCTG ATCCAGAAGG
 151 CCAGCTGGCT TCTCCTGAGC TACTTTCAAT TCGCAGCAAC CACTGATCCT
 201 GGTCCAGGTG ACTGGGGAAG ACGCTGAGGG TATAAACCCA AACATTGAAC
 251 CTGAAGACCC AGCGCAAAGT AGAAACTGAA AGTACCCTGC TTACTCTGCC
 301 GGCAGATCCT ACGGAAGTTA TGGCAAAGCC AGAGCGCCTG GGTGGCCGGT
 351 GATGCATGCG GCCCTCTTG GGATGGATGG ACCAGGCGTG GCGTGGGTGA
 401 GAGGAGTCAG CTGCCTGAAC TGCCCTGCCC AGCACCGGTT TGCGGCCACC
 451 CGGTGGATGA CCGGGGTCCT GGGAGTGATT ATGGGTGGTG AGAGCCGGCT
 501 CCTGCTGCAG TCCCAGTCAT CATGACTACA CCCACCTCCC GCAGACCATG
 551 TTCCATGTTT CTTTTAGATA TATCTTTGGA ATTCCTCCAC TGATCCTTGT
 601 TCTGCTGCCT GTCACATCAT CTGAGTGCCA CATTAAAGAC AAAGAAGGTA
 651 AAGCATATGA GAGTGTACTG ATGATCAGCA TCGATGAATT GGACAAAATG
 701 ACAGGAACTG ATAGTAATTG CCCGAATAAT GAACCAAACT TTTTTAGAAA
 751 ACATGTATGT GATGATACAA AGGAAGCTGC TTTTCTAAAT CGTGCTGCTC
 801 GCAAGTTGAA GCAATTTCTT AAAATGAATA TCAGTGAAGA ATTCAATGTC
 851 CACTTACTAA CAGTATCACA AGGCACACAA ACACTGGTGA ACTGCACAAG
 901 TAAGGAAGAA AAAAACGTAA AGGAACAGAA AAAGAATGAT GCATGTTTCC
 951 TAAAGAGACT ACTGAGAGAA ATAAAAACTT GTTGGAATAA AATTTTGAAG
1001 GGCAGTATAT AAACAGGACA TGTAGTAACA ACCTCCAAGA ATCTACTGGT
1051 TCATATACTT GGAGAGGTTG AAACCCTTCC AGAAGTTCCT GGATGCCTCC
1101 TGCTCAAATA AGCCAAGCAG CTGAGAAATC TACAGTGAGG TATGAGATGA
1151 TGGACACAGA AATGCAGCTG ACTGCTGCCG TCAGCATATA CATATAAAGA
1201 TATATCAACT ATACAGATTT TTGTAATGCA ATCATGTCAA CTGCAATGCT
1251 TTTAAAACCG TTCCAAATGT TTCTAACACT ACAAAGTCTA CAAAAAGCAA
1301 GGCTATGAAG ATTCAGAGTC ACCACTGTTT TCTTAGCAAA ATGATGGTAT
1351 GGTTAAACAT TCATTGGTGA ACCACTGGGG GAGTGGAACT GTCCTGTTTT
1401 AGACTGGAGA TACTGGAGGG CTCACGGTGA TGGATAATGC TCTTGAAAAC
1451 AAGAGTCTAT CTTAAAGCAG CAGCAAAAAG AAGCTTAAGG CACTTAAGGC
1501 AGCAACAAAT GTAGTTAAAT ATGAATGTAT AACACATAAC TTCAGTAAAG
1551 AGCATAGCAG ATATTTTTAA ATAAAAGTAT TTTTAAAGAT AAAAAAAAAA
1601 AAAAAA
```

FIGURE 3:

```
ATG TTC CAT GTT TCT TTT AGA TAT ATC TTT GGA ATT CCT CCA CTG    -31
Met Phe His Val Ser Phe Arg Tyr Ile Phe Gly Ile Pro Pro Leu    -11

ATC CTT GTT CTG CTG CCT GTC ACA TCA TCT GAG TGC CAC ATT AAA     15
Ile Leu Val Leu Leu Pro Val Thr Ser Ser Glu Cys His Ile Lys      5

GAC AAA GAA GGT AAA GCA TAT GAG AGT GTA CTG ATG ATC AGC ATC     60
Asp Lys Glu Gly Lys Ala Tyr Glu Ser Val Leu Met Ile Ser Ile     20

GAT GAA TTG GAC AAA ATG ACA GGA ACT GAT AGT AAT TGC CCG AAT    105
Asp Glu Leu Asp Lys Met Thr Gly Thr Asp Ser Asn Cys Pro Asn     35

AAT GAA CCA AAC TTT TTT AGA AAA CAT GTA TGT GAT GAT ACA AAG    150
Asn Glu Pro Asn Phe Phe Arg Lys His Val Cys Asp Asp Thr Lys     50

GAA GCT GCT TTT CTA AAT CGT GCT GCT CGC AAG TTG AAG CAA TTT    195
Glu Ala Ala Phe Leu Asn Arg Ala Ala Arg Lys Leu Lys Gln Phe     65

CTT AAA ATG AAT ATC AGT GAA GAA TTC AAT GTC CAC TTA CTA ACA    240
Leu Lys Met Asn Ile Ser Glu Glu Phe Asn Val His Leu Leu Thr     80

GTA TCA CAA GGC ACA CAA ACA CTG GTG AAC TGC ACA AGT AAG GAA    285
Val Ser Gln Gly Thr Gln Thr Leu Val Asn Cys Thr Ser Lys Glu     95

GAA AAA AAC GTA AAG GAA CAG AAA AAG AAT GAT GCA TGT TTC CTA    330
Glu Lys Asn Val Lys Glu Gln Lys Lys Asn Asp Ala Cys Phe Leu    110

AAG AGA CTA CTG AGA GAA ATA AAA ACT TGT TGG AAT AAA ATT TTG    375
Lys Arg Leu Leu Arg Glu Ile Lys Thr Cys Trp Asn Lys Ile Leu    125

AAG GGC AGT ATA TAA                                            387
Lys Gly Ser Ile End                                            129
```

FIGURE 4:

```
   1 GAATTCCTCT GGTCCTCATC CAGGTGCGCG GGAAGCAGGT GCCCAGGAGA
  51 GAGGGGATAA TGAAGATTCC ATGCTGATGA TCCCAAAGAT TGAACCTGCA
 101 GACCAAGCGC AAAGTAGAAA CTGAAAGTAC ACTGCTGGCG GATCCTACGG
 151 AAGTTATGGA AAAGGCAAAG CGCAGAGCCA CGCCGTAGTG TGTGCCGCCC
 201 CCCTTGGGAT GGATGAAACT GCAGTCGCGG CGTGGGTAAG AGGAACCAGC
 251 TGCAGAGATC ACCCTGCCCA ACACAGACTC GGCAACTCCG CGGAAGACCA
 301 GGGTCCTGGG AGTGACTATG GGCGGTGAGA GCTTGCTCCT GCTCCAGTTG
 351 CGGTCATCAT GACTACGCCC GCCTCCCGCA GACCATGTTC CATGTTTCTT
 401 TTAGGTATAT CTTTGGACTT CCTCCCCTGA TCCTTGTTCT GTTGCCAGTA
 451 GCATCATCTG ATTGTGATAT TGAAGGTAAA GATGGCAAAC AATATGAGAG
 501 TGTTCTAATG GTCAGCATCG ATCAATTATT GGACAGCATG AAAGAAATTG
 551 GTAGCAATTG CCTGAATAAT GAATTTAACT TTTTTAAAAG ACATATCTGT
 601 GATGCTAATA AGGAAGGTAT GTTTTTATTC CGTGCTGCTC GCAAGTTGAG
 651 GCAATTTCTT AAAATGAATA GCACTGGTGA TTTTGATCTC CACTTATTAA
 701 AAGTTTCAGA AGGCACAACA ATACTGTTGA ACTGCACTGG CCAGGTTAAA
 751 GGAAGAAAAC CAGCTGCCCT GGGTGAAGCC CAACCAACAA AGAGTTTGGA
 801 AGAAAATAAA TCTTTAAAGG AACAGAAAAA ACTGAATGAC TTGTGTTTCC
 851 TAAAGAGACT ATTACAAGAG ATAAAAACTT GTTGGAATAA AATTTTGATG
 901 GGCACTAAAG AACACTGAAA AATATGGAGT GGCAATATAG AAACACGAAC
 951 TTTAGCTGCA TCCTCCAAGA ATCTATCTGC TTATGCAGTT TTTCAGAGTG
1001 GAATGCTTCC TAGAAGTTAC TGAATGCACC ATGGTCAAAA CGGATTAGGG
1051 CATTTGAGAA ATGCATATTG TATTACTAGA AGATGAATAC AAACAATGGA
1101 AACTGAATGC TCCAGTCAAC AAACTATTTC TTATATATGT GAACATTTAT
1151 CAATCAGTAT AATTCTGTAC TGATTTTTGT AAGACAATCC ATGTAAGGTA
1201 TCAGTTGCAA TAATACTTCT CAAACCTGTT TAAATATTTC AAGACATTAA
1251 ATCTATGAAG TATATAATGG TTTCAAAGAT TCAAAATTGA CATTGCTTTA
1301 CTGTCAAAAT AATTTTATGG CTCACTATGA ATCTATTATA CTGTATTAAG
1351 AGTGAAAATT GTCTTCTTCT GTGCTGGAGA TGTTTTAGAG TTAACAATGA
1401 TATATGGATA ATGCCGGTGA GAATAAGAGA GTCATAAACC TTAAGTAAGC
1451 AACAGCATAA CAAGGTCCAA GATACCTAAA AGAGATTTCA AGAGATTTAA
1501 TTAATCATGA ATGTGTAACA CAGTGCCTTC AATAAATGGT ATAGCAAATG
1551 TTTTGACATG AAAAAAGGAC AATTTCAAAA AAAAAAAA
```

FIGURE 5:

| | | | | | | | | | | | | |
|---|---|---|---|---|---|---|---|---|---|---|---|---|
| ATG | TTC | CAT | GTT | TCT | TTT | AGG | TAT | ATC | TTT | GGA | CTT | CCT | CCC | CTG | -31 |
| Met | Phe | His | Val | Ser | Phe | Arg | Tyr | Ile | Phe | Gly | Leu | Pro | Pro | Leu | -11 |

```
ATG TTC CAT GTT TCT TTT AGG TAT ATC TTT GGA CTT CCT CCC CTG  -31
Met Phe His Val Ser Phe Arg Tyr Ile Phe Gly Leu Pro Pro Leu  -11

ATC CTT GTT CTG TTG CCA GTA GCA TCA TCT GAT TGT GAT ATT GAA   15
Ile Leu Val Leu Leu Pro Val Ala Ser Ser Asp Cys Asp Ile Glu    5

GGT AAA GAT GGC AAA CAA TAT GAG AGT GTT CTA ATG GTC AGC ATC   60
Gly Lys Asp Gly Lys Gln Tyr Glu Ser Val Leu Met Val Ser Ile   20

GAT CAA TTA TTG GAC AGC ATG AAA GAA ATT GGT AGC AAT TGC CTG  105
Asp Gln Leu Leu Asp Ser Met Lys Glu Ile Gly Ser Asn Cys Leu   35

AAT AAT GAA TTT AAC TTT TTT AAA AGA CAT ATC TGT GAT GCT AAT  150
Asn Asn Glu Phe Asn Phe Phe Lys Arg His Ile Cys Asp Ala Asn   50

AAG GAA GGT ATG TTT TTA TTC CGT GCT GCT CGC AAG TTG AGG CAA  195
Lys Glu Gly Met Phe Leu Phe Arg Ala Ala Arg Lys Leu Arg Gln   65

TTT CTT AAA ATG AAT AGC ACT GGT GAT TTT GAT CTC CAC TTA TTA  240
Phe Leu Lys Met Asn Ser Thr Gly Asp Phe Asp Leu His Leu Leu   80

AAA GTT TCA GAA GGC ACA ACA ATA CTG TTG AAC TGC ACT GGC CAG  285
Lys Val Ser Glu Gly Thr Thr Ile Leu Leu Asn Cys Thr Gly Gln   95

GTT AAA GGA AGA AAA CCA GCT GCC CTG GGT GAA GCC CAA CCA ACA  330
Val Lys Gly Arg Lys Pro Ala Ala Leu Gly Glu Ala Gln Pro Thr  110

AAG AGT TTG GAA GAA AAT AAA TCT TTA AAG GAA CAG AAA AAA CTG  375
Lys Ser Leu Glu Glu Asn Lys Ser Leu Lys Glu Gln Lys Lys Leu  125

AAT GAC TTG TGT TTC CTA AAG AGA CTA TTA CAA GAG ATA AAA ACT  420
Asn Asp Leu Cys Phe Leu Lys Arg Leu Leu Gln Glu Ile Lys Thr  140

TGT TGG AAT AAA ATT TTG ATG GGC ACT AAA GAA CAC TGA          456
Cys Trp Asn Lys Ile Leu Met Gly Thr Lys Glu His End          152
```

INTERLEUKIN-7

CROSS-REFERENCE TO RELATED APPLICATION

This application is a continuation of U.S. patent application Ser. No. 07/511,438, filed Apr. 13, 1990, now abandoned, which is a division of application Ser. No. 07/255,209, filed Oct. 7, 1989, now U.S. Pat. No. 4,965,195 and a continuation-in-part of U.S. patent application Ser. No. 113,566, filed Oct. 26, 1987, now abandoned.

BACKGROUND OF THE INVENTION

The present invention relates generally to the fields of immunology and molecular biology, and particularly to a polypeptide growth factor which regulates the proliferation and differentiation of lymphocyte and other hematopoietic progenitors.

B and T lymphocytes are the primary effector cells of the immune responses. Both cell classes are considered to derive ultimately from hematopoietic stem cells in the mammalian bone marrow, via progenitor or precursor cells representing distinguishable stages in the differentiation of each class.

B lymphocytes, or B cells, are the precursors of circulating antibody-secreting plasma cells. Mature B cells, which are characterized by expression of surface-bound immunoglobulin capable of binding specific antigens, derive from hematopoietic stem cells via an intermediary cell class known as pre-B cells. Mature T cells develop principally in the thymus, presumably from an as-yet-unidentified precursor cell which migrates from the bone marrow to the thymus at an early stage of T lymphocyte development.

While considerable progress has been made in identifying soluble hormone-like factors which regulate differentiation of other cells of hematopoietic origin, for example, granulocytes and macrophages, very little is known about regulatory factors involved in B and T cell lymphogenesis. The pluripotent lymphoid stem cell has not been identified, nor have all of the factors or conditions required for commitment and expansion of the B and T cell lineages been defined. The later stages of B and T cell growth and differentiation, following the appearance of surface immunoglobulin and the emergence of the B cell from the bone marrow, or the T cell from the thymus, have been the most well studied. This work has revealed a number of factors which are active on mature peripheral B and T cells, including IL-1, IL-2, IL-4, IL-5, interferon gamma, BSF-2, neuroleukin, and transforming growth factor beta.

Fragmentary evidence has been made available concerning the B cells considered to be the immediate precursors of mature functional peripheral B cells. These pre-B cells have been defined as cells containing cytoplasmic $\mu$ chain but no cytoplasmic light chain and no surface immunoglobulin.

Paige, *Nature* 302:711 (1983) and Paige et al., *Eur. J. Immunol.* 14:979 (1984) described techniques for culturing B cell progenitors derived from 14-day murine fetal liver cells. These pre-B cells were observed to differentiate to antibody secreting B cells in vitro when cultures were supported by a layer of fetal liver cells, bone marrow adherent cells, or conditioned media containing colony stimulating factors.

Giri et al., *J. Immunol.* 132:223 (1984) cultured a murine bone marrow-derived pre-B cell line, 70z/3, in the presence of partially purified IL-1 preparations derived from lipopolysaccharide (LPS) induced P388D1 cell supernatants. Following contact with the IL-1 preparation, the pre-B cells were observed to express surface immunoglobulin. Jyonouchi et al., *J. Immunol.* 135:1891 (1985) reported that a humoral factor or factors from the serum of NZB mice could enhance the maturation of B lineage precursor cells. Landreth et al., *J. Immunol.* 134:2305 (1985) demonstrated that a factor (or factors) present in the urine of a cyclic neutropenic patient stimulated generation of pre-B cells in human and mouse bone marrow cultures.

However, these results have been difficult to interpret due to the non-homogeneous nature of the cell populations involved. The pleiotropic effects of known lymphokines, as well as their potent intrinsic biological activities, complicate analysis of assays involving the response of heterogeneous cell cultures to conditioned cell culture media derived from serum-containing cell cultures.

One major impediment to the study of lymphocyte development has been the difficulty associated with obtaining enriched populations of viable lymphoid precursors. The long term bone marrow culture system developed by Whitlock and Witte, *J. Immunol. Meth.* 67:353 (1984) has provided a source of pre-B cells for study. In a Whitlock-Witte culture, an adherent support layer comprising stromal-derived fibroblasts, macrophages, and endothelial cells is employed as a feeder layer to support the growth of an upper phase of nonadherent pre-B and earlier lymphoid precursors.

Whitlock et al., *Cell* 48:1009 (1987), and Hunt et al., *Cell* 48:997 (1987) reported cloning of cell lines derived from murine bone marrow stroma which were capable of supporting growth of pre-B cells and other precursors of mature B cells in Whitlock-Witte cultures. Supernatants of one such cell line, designated ALC, were tested for activity in IL-1, IL-2, IL-3, and IL-4 assays. The absence of activity in these assays suggested that these factors were not the source of the proliferation-inducing activity found in ALC supernatants. Both Whitlock et al. and Hunt et al. considered the pre-B cell inducing activity which they observed to be attributable to a novel factor present in the stromal cell supernatants.

In developing the present invention, a variant of the Whitlock-Witte culture system was employed as a source of immature B cells, which were the basis for a rapid quantitative assay for detecting growth factors capable of stimulating proliferation of pre-B cells. A putative factor observed in murine stromal cell cultures was tentatively designated "Lymphopoietin-1" ("LP-1"), and subsequently designated "Interleukin-7" ("IL-7"). To clone a murine IL-7 cDNA, which was used to secure the human cDNA, a new cloning technique was employed. To obtain a cell line which expressed a soluble murine IL-7 in detectable quantities, a novel cell line was established by transformation of stromal cells derived from a Whitlock-Witte culture. This cell line, which secretes a pre-B cell growth activity in serum-free media, provided specific IL-7 messenger RNA for expression cloning, and protein for purification and sequencing. Isolation of a murine cDNA clone enabled identification by cross-hybridization of human genomic and cDNA clones encoding human IL-7.

Preliminary experiments involving administration of purified recombinant IL-7 to mice have indicated that in addition to stimulating the development and proliferation of the hematopoietic precursors of T and B cells, IL-7 is also capable of inducing the proliferation of megakaryocyte and granulocyte/macrophage precursors in bone marrow. In view of potential immunological therapeutic uses in stimulating proliferation of precursors of T cells and antibody-secreting B cells, as well as other hematopoietic cell types, there is considerable interest in developing technology for producing biologically active IL-7 molecules. Use of recombinant expression systems can provide sufficient quantities of pure protein to permit detailed study of the biological activity of such molecules and to supply anticipated clinical demands for therapeutic IL-7 compositions.

SUMMARY OF THE INVENTION

The present invention provides mammalian Interleukin-7 (IL-7) proteins, previously designated Lymphopoietin-1 ("LP-1"). These molecules can be prepared by purification from cell culture supernatants or by expression of DNA sequences encoding a mammalian IL-7. Preferably, such sequences consist essentially of a single open reading frame nucleotide sequence capable of being expressed in a recombinant transcriptional unit under the control of mammalian, microbial, or viral transcriptional or translational control elements. The present invention also provides recombinant expression vectors comprising the DNA sequences, eukaryotic and prokaryotic expression systems comprising the recombinant expression vectors, processes for making the proteins by purification from mammalian cell culture media or by recombinant expression in appropriate eukaryotic or prokaryotic systems, various therapeutic compositions and methods comprising or involving use of the proteins of the invention, and antibodies which are immunoreactive with the proteins of the invention.

BRIEF DESCRIPTION OF THE FIGURES

FIG. 2 illustrates the nucleotide sequence of a cDNA clone encoding murine IL-7 (mIL-7), which was identified by direct expression cloning using a mammalian expression vector. The initiation codon of the full-length native protein, the codon specifying the N-terminal amino acid of the mature sequence, and termination codon are underlined.

FIG. 3 indicates the nucleotide sequence and derived amino acid sequence of the coding region of the murine cDNA clone of FIG. 2. The mature protein sequence is encoded by the nucleotide sequence beginning at nucleotide 1 and ending at nucleotide 387. The presumed signal peptide encoded as a leader sequence of the native translation product is encoded by nucleotides $-75$ to $-1$. The N-terminal glutamic acid residue of mature mIL-7 is underlined.

FIG. 4 illustrates the nucleotide sequence of a cDNA clone encoding human IL-7 (hIL-7), which was isolated by cross-hybridization studies using a probe derived from the mIL-7 cDNA. The initiation codon of the full-length native protein, the condon specifying the N-terminal amino acid of the mature sequence, and termination codon are underlined.

FIG. 5 indicates the nucleotide sequence and derived amino acid sequence of the coding region of the hIL-7 cDNA clone of FIG. 4. The mature human protein is encoded by the sequence beginning at nucleotide 1 and ending at nucleotide 456. A putative hydrophobic signal peptide encoded as a leader sequence of the native translation product is encoded by nucleotides $-75$ to $-1$. The N-terminal aspartic acid residue of the mature protein is underlined. A plasmid bearing the coding sequence of hIL-7 in *E. coli* strain JM107 was deposited with the American Type Culture Collection on Oct. 21, 1987, and assigned accession number ATCC 67546.

DETAILED DESCRIPTION OF THE INVENTION

1. Definitions

Figure 1:
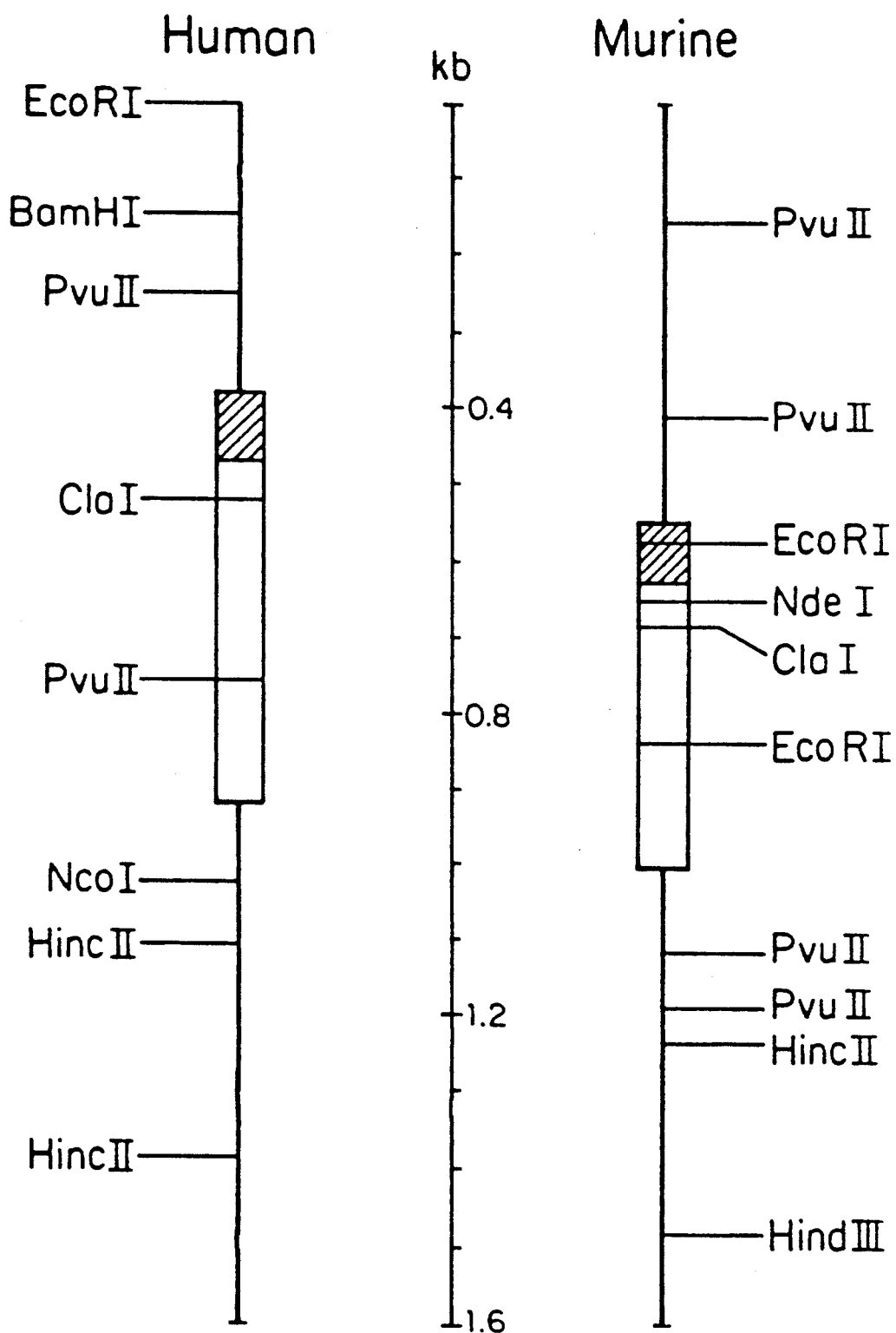
FIG. 1 provides restriction maps of cDNA clones encoding human and murine IL-7 proteins. The blocks indicate the positions of the open reading frames; crosshatching indicates a signal peptide or leader sequence. The approximate positions of selected restriction endonuclease recognition sites are marked.

"Interleukin-7" and "IL-7" refer to a mammalian endogenous secretory protein which is capable of inducing proliferation of bone marrow-derived lymphocyte progenitors and precursors, including the specialized precursors known as pre-B cells. Alternative designations for this molecule are "pre-B cell growth factor" and "lymphopoietin-1". The predicted molecular weight of the mature murine protein corresponding to the sequence depicted in FIG. 3 is 14,897 daltons, exclusive of any glycosylation. The predicted molecular weight of the mature human protein corresponding to the sequence depicted in FIG. 5 is 17,387 daltons, exclusive of glycosylation. As used throughout the specification, the term "mature" means a protein expressed in a form lacking a leader sequence as may be present in full-length transcripts of a native gene.

"Substantially homologous" or "substantially identical", which can refer both to nucleic acid and amino acid sequences, means that a particular subject sequence, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 90 percent similarity, equivalent biological activity, and equivalent expression characteristics are considered substantially identical or homologous, and are included within the scope of proteins defined by the term "Interleukin-7." Amino acid sequences having greater than 40 percent similarity are considered substantially similar. In defining nucleic acid sequences, all subject nucleic acid sequences capable of encoding substantially homologous or similar amino acid sequences are considered substantially homologous or similar to a reference nucleic acid sequence. For purposes of determining homology or similarity, truncation or internal deletions of the reference sequence should be disregarded. Sequences having lesser degrees of homology and comparable bioactivity are considered equivalents. For purposes of the present invention, a "subunit" of an IL-7 protein is deemed to constitute an amino acid sequence of at least 20 amino acids.

"Recombinant," as used herein, means that a protein is derived from recombinant (e.g., microbial or mammalian) expression systems, which can involve transformation of cells of any species by techniques known to those of skill in the art. "Microbial" refers to recombinant proteins made in bacterial or fungal (e.g., yeast) expression systems. As a product, "recombinant microbial" defines a protein essentially free of native endogenous substances and unaccompanied by associated native glycosylation. Protein expressed in most bacterial cultures, e.g., E. coli, will be free of glycan; protein expressed in yeast will have a glycosylation pattern different from that expressed in mammalian cells.

"Isolated DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such isolated sequences are preferably provided in the form of an open reading frame uninterrupted by internal nontranslated sequences, or introns, which are typically present in eukaryotic genes. Sequences of non-translated DNA may be present downstream from the open reading frame, where the same do not interfere with manipulation or expression of the coding regions. "Nucleotide sequence" refers to a heteropolymer of deoxyribonucleotides. Generally, DNA sequences encoding the proteins provided by this invention are assembled from cDNA fragments and short oligonucleotide linkers, or from a series of oligonucleotides, to provide a synthetic gene which is capable of being expressed in a recombinant transcriptional unit. IL-7 DNAs can also be isolated from the genomic DNA of any mammalian cell.

"Recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural elements intended for use in yeast expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product. Vectors potentially useful in expression of biologically active IL-7 proteins also include viruses, e.g., phage, or DNA fragments integratable into the host genome by recombination.

"Recombinant microbial expression system" means a substantially homogeneous monoculture of suitable host microorganisms, for example, bacteria such as E. coli or yeast such as S. cerevisiae, which have stably integrated a recombinant transcriptional unit into chromosomal DNA or carry the recombinant transcriptional unit as a component of a resident plasmid. Generally, cells constituting the system are the progeny of a single ancestral transformant. Recombinant expression systems as defined herein will express heterologous protein upon induction of the regulatory elements linked to the DNA sequence or synthetic gene to be expressed.

2. Development of IL-7 Assay and Cellular Sources of Factor

An in vitro culture system for B cell precursors was employed to identify a factor secreted in cell culture by murine bone marrow stromal cells which regulates pre-B cell growth. The observed strict growth dependence of pre-B cells upon their stromal feeder layers in Whitlock-Witte cultures suggested that the stromal cells produced a pre-B cell growth stimulatory activity. In order to characterize this growth activity, a quantitative assay was developed and a cellular source of the pre-B cell growth promoting activity was sought.

Initial attempts to develop a bioassay utilized cell-free supernatants from long-term stromal bone marrow (feeder) layers as a source of growth promoting activity. Generally the assay results were equivocal, because a stimulation index of only two to four fold over background was observed. This is consistent with the results reported by Whitlock et al., Cell 48:1009 (1987), and Hunt et al., Cell 48:997 (1987). In order to circumvent this obstacle and establish a suitable cellular source of growth factor, an immortalized cell line was generated by transfecting stromal cells from long term bone marrow cultures with the pSV3neo plasmid containing the SV40 T antigen transforming sequences. One resulting clonal cell line, designated I×N/A6, was found to constitutively produce a factor capable of supporting the growth of precursor B cells. Subsequently, it was found that comparable levels of pre-B cell growth promoting activity could be produced when the cells were grown under serum-free conditions in the presence of 1 $\mu$g/ml LPS.

In order to optimize assay sensitivity, a highly enriched population of precursor B cells was obtained from long term bone marrow cultures. A further cell enrichment step employing passage over G-10 Sephadex was used to obtain a more homogeneous population capable of generating suitable biological assay results. The specificity of this assay system was tested with other defined factors. No factor tested, including IL-1$\beta$, IL-1$\beta$, IL-2, IL-3, IL-4, IL-5, GM-CSF, G-CSF, CSF-1, BSF-2, alpha, beta, and gamma interferon, neuroleukin, and transforming growth factor beta, was capable of inducing stimulation of thymidine incorporation over background levels throughout a range of factor concentrations. In addition, purified mIL-7 did not elicit any response in standard bioassays for IL-1, IL-2, IL-3, GM-CSF (FDCP$_2$-1D), IL-4, IL-5, G-CSF, CSF-1 and interferon. However, cell free supernatants from the I×N/A6 cell line did stimulate formation of murine macrophage-type colonies in soft agar. Fractionation of I×N/A6 conditioned medium by DEAE-Sephacel chromatography resolved the colony stimulating activity from the pre-B cell growth promoting activity. A preferred assay protocol for IL-7 activity is described below.

3. Assay for IL-7 Biological Activity

To establish a pre-B cell precursor population, bone marrow cultures were initiated and maintained as described by Whitlock et al., J. Immunol. Meth. 67:353 (1983), in RPMI 1640 supplemented with a selected lot of 5% fetal bovine serum (FBS) (Irvine Scientific, Santa Clara, Calif., USA), 50 μM 2-mercaptoethanol, 50 U/ml penicillin, 50 μg/ml streptomycin and 2 mM L-glutamine.

The non-adherent hematopoietic cells obtained from this type of culture system have been shown to include B progenitor cells, pre-B cells, and some early B cells. See Whitlock et al., Cell 32:903 (1983). Significantly, Dorshkind et al., J. Immunol. 137:3457 (1986), demonstrated that cells from such bone marrow cultures were capable of reconstituting both the B cell and the T cell compartments in combined immunodeficient mice, indicating that a lymphoid stem cell element may also be present in these cultures. At present, the complete repertoire of responsive cells has not been determined, but clearly this population includes precursor cells of the B lineage. These cells exhibit a lymphocytic appearance with a large nucleus and a small rim of cytoplasm which is consistent with a pre-B cell phenotype.

For assay, non-adherent pre-B cells are removed from adherent stromal layers of Whitlock-Witte cultures by gentle pipetting, pelleted by centrifugation, and resuspended in 1-2 ml of Iscoves modified Dulbeccos Medium (IMDM) containing 5% FBS, 50 U/ml penicillin, 50 μg/ml streptomycin and 2 mM L-glutamine (assay medium).

The cells are then applied to a small column of Sephadex G-10 (trademark of Pharmacia Fine Chemicals, Inc., Uppsala, SE, for gel filtration media) at a density of less than $10^8$ cells per ml gel, to remove any dislodged, contaminating adherent or stromal cells, and then incubated at room temperature for 10 minutes, as described by Ly et al., J. Immunol. Meth. 5:239 (1974). The pre-B cells are then eluted from the G10 column with assay medium, washed, and resuspended at a density of $2.5 \times 10^5$ cells/ml in assay medium. Samples to be assayed are serially diluted in individual wells of a 96 well microtiter plate in a final volume of 50 ml. Fifty microliters of the cell suspension (12,500 cells/well) are added to each well and the plates are incubated for 48 hours in a humidified $CO_2$ incubator containing 7.5% $CO_2$, 5% $O_2$, balance $N_2$. The cultures are pulsed during the final four hours of incubation with 2 μCi/well of tritiated thymidine ($^3$H-TdR; NEN, 60-80 Ci/mmole) in a volume of 25 microliters. Cultures are harvested with an automated harvester onto glass fiber filters and incorporated radioactivity determined by liquid scintillation counting. One unit of IL-7 is defined as the amount of factor required to induce half-maximal $^3$H-TdR incorporation under the conditions of the IL-7 assay described above.

Figure 6A:
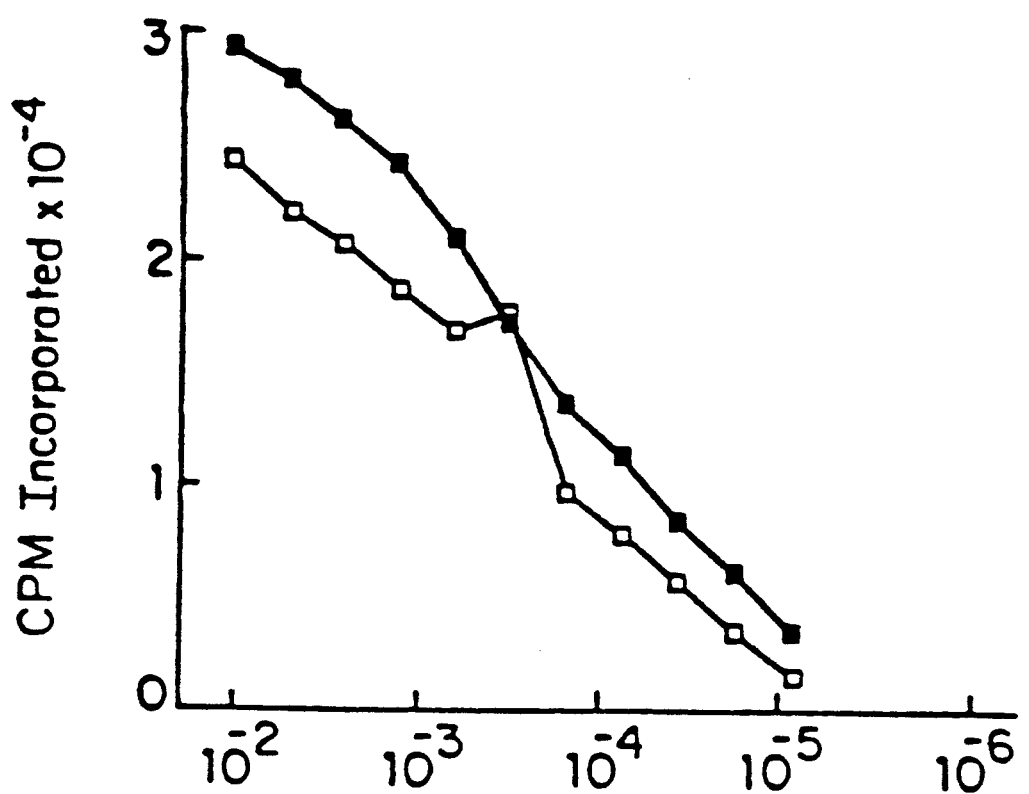
FIGS. 6a and 6b indicates the response of pre-B cells (Panel A) and thymocytes (Panel B) to IL-7. In the experiment depicted in Panel A, pre-B cells from Whitlock-Witte bone marrow cultures (see below) were cultured at a density of $2.5 \times 10^5$ cells per ml in the presence of IL-7 for three days at 37° C. Two sources of IL-7 were employed: serial dilutions of supernatant from COS-7 cells transfected with an expression vector containing the IL-7 gene (open squares), and purified recombinant IL-7 protein, beginning at a 100 ng/ml concentration (solid squares). In the experiment depicted in Panel B, thymocytes were cultured at a density of $1 \times 10^7$ cells per ml under the same conditions, except that dilutions of purified recombinant IL-7 protein were initiated at a 1 μg/ml concentration. In all experiments, each plotted value represents the mean of triplicate samples.
Figure 6B:
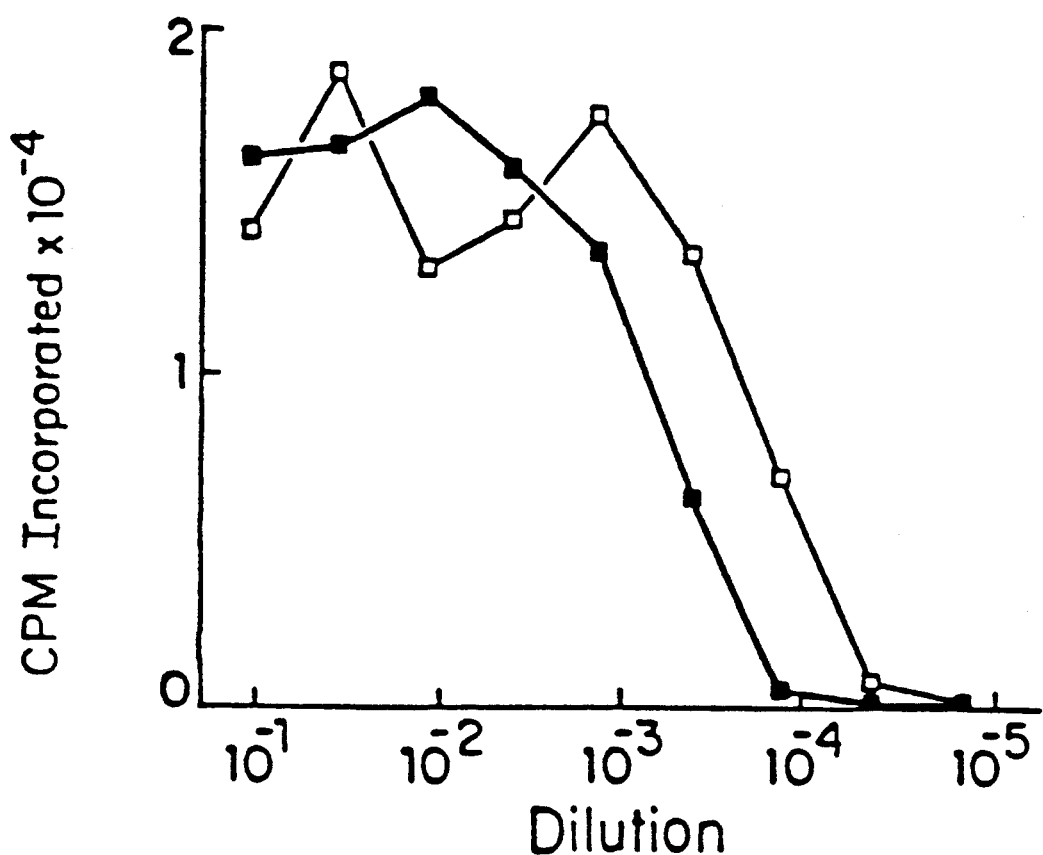

The results of typical pre-B cell proliferation assays employing crude and purified preparations of recombinant IL-7 are depicted in FIG. 6, Panel A.

4. Isolation of Purified Native Protein

Development of purification methods for murine IL-7 revealed that the biological activity of the factor is stable in a wide spectrum of conditions that included extremes of pH (2.1 to 9.0) and solutions containing the organic solvents acetonitrile or n-propanol. Resolution of the activity by SDS-PAGE (sodium dodecyl sulfate polyacrylamide gel electrophoresis) indicated that the IL-7 activity was associated with a protein of $M_r$ 25,000 and was stable in the presence of SDS and temperatures of 70° C. However, reduction of the protein by contact with 1% 2-mercaptoethanol completely destroyed its biological activity, indicating the presence of intramolecular disulfide bonds. Preparative SDS-PAGE resolved a single protein of $M_r$ 25,000 that coincided with the biological activity. Moreover, radiolabeled IL-7 bound specifically to cells that respond to this factor, suggesting that IL-7, like other polypeptide hormones, binds to specific receptors on the surface of cells. The purification protocol resulted in a 10 million fold purification with a final yield of 35%. An N-terminal sequence obtained by Edman degradation was X-X-His-Ile-Lys-Asp-Lys-Glu-X-Lys-Ala-Tyr-Glu-X-Val-Met, which was unique when compared to a database of published protein sequences.

The purified IL-7 exhibited an estimated specific activity of about $4 \times 10^6$ units/μg protein and was active at a concentration of $10^{-1}$ pM, based upon visual estimates of protein concentration determined by the intensity of silver stained SDS-PAGE. This initial estimate of specific activity in the pre-B cell proliferation assay has been revised downward in light of more accurate determinations of protein concentrations. The specific activity of purified recombinant IL-7 in the pre-B cell proliferation assay appears to be in the range of $1-2 \times 10^5$ units/μg.

5. Isolation of cDNAs

In order to secure the murine coding sequence, a DNA sequence encoding mIL-7 was isolated from a cDNA library prepared by reverse transcription of polyadenylated RNA isolated from the transformed murine stromal cell line I×N/A6. The library was screened by direct expression of pooled cDNA fragments in monkey COS-7 cells using a mammalian expression vector (pDC201) that uses regulatory sequences derived from SV40 and Adenovirus 2. Approximately 720,000 cDNAs were screened in pools of approximately 1000 cDNAs until assay of the supernatant of one transfectant pool detected a tenfold increase in thymidine incorporation over background. A frozen stock of bacteria from this positive pool was then used to obtain plates of approximately 200 colonies. Plasmid DNA from the colonies on each of these plates was pooled and transformed into COS-7 cells and a positive pool was identified. Individual colonies from this pool were screened until a single clone was identified which directed synthesis of a 25 kilodalton protein with detectable IL-7 activity. This clone was isolated, and its insert sequenced to determine the coding sequence of the murine cDNA set forth in FIG. 2. This cDNA includes a lengthy 548 base pair non-translated region adjacent to the translation initiation site. The starting site for the mature protein was deduced by comparison to an N-terminal amino acid sequence obtained from highly purified preparations of IL-7 derived from A6 cell supernatants. The coding region contains six cysteine residues and two potential N-glycosylation sites.

Probes were constructed from the murine sequence and used to screen human genomic DNA libraries and human cDNA libraries derived from cultures of the human liver adenocarcinoma cell line SK-HEP-1 (ATCC HTB-52). cDNA clones which hybridized to oligonucleotide probes derived from human genomic sequences and probes comprising selected 3' and 5' nontranslated sequences of the murine gene were then isolated and sequenced. The full cDNA sequence thus isolated is depicted in FIG. 4, and the derived coding sequence is depicted in FIG. 5.

Human IL-7 is coded by a multi-exon gene. In isolating the cDNA clone described in FIG. 4, several alternative mRNA constructs were observed which can be attributed to different mRNA splicing events following transcription. These alternative constructs, which share large regions of homology with the cDNAs specifically claimed herein, are considered to be within the scope of the present invention.

6. Synthetic DNA Constructions

In its nucleic acid embodiments, the present invention provides DNA sequences encoding mammalian IL-7s, IL-7 analogs and subunits. Examples of mammalian IL-7s include primate IL-7, human IL-7, murine, canine, feline, equine, bovine, porcine, ovine, cervine, and caprine IL-7s. IL-7 DNAs are preferably provided in a form which is capable of being expressed in a recombinant transcriptional unit under the control of mammalian, microbial, or viral transcriptional or translational control elements. For example, a sequence to be expressed in a microorganism will contain no introns. In preferred aspects, the DNA sequences comprise at least one, but optionally more than one, sequence component derived from a cDNA sequence or copy thereof. Such sequences may be linked or flanked by DNA sequences prepared by assembly of synthetic oligonucleotides. Exemplary sequences include those substantially homologous to the nucleotide sequences depicted in FIG. 3 and FIG. 5. Optionally, the coding sequences may include codons encoding one or more additional amino acids located at the N-terminus, for example, an N-terminal ATG codon specifying methionine linked in reading frame with the nucleotide sequence. Due to code degeneracy, there can be considerable variation in nucleotide sequences encoding the same amino acid sequence; one exemplary DNA embodiment is that corresponding to the sequence of nucleotides 1-387 of FIG. 3. Synthetic DNA sequences encoding IL-7 proteins which include nucleotide sequences altered to introduce restriction sites or preferred codon usage for bacterial expression are included within the scope of the invention.

The present invention also provides expression vectors for producing useful quantities of purified IL-7, which can comprise synthetic or cDNA-derived DNA fragments encoding mammalian IL-7s or IL-7 analogs or subunits operably linked to regulatory elements derived from mammalian, bacterial, yeast, bacteriophage, or viral genes. Useful regulatory elements are described in greater detail below. Following transformation or transfection of appropriate cell lines, such vectors can be induced to express recombinant protein.

7. Recombinant Expression Systems

Mammalian IL-7s can be expressed in mammalian or insect cells, yeast, bacteria, or other cells under the control of appropriate promoters. Cell-free translation systems could also be employed to produce mammalian IL-7 using RNAs derived from the DNA constructs of the present invention. Appropriate cloning and expression vectors for use with bacterial, fungal, yeast, and mammalian cellular hosts are described by Pouwels et al., *Cloning Vectors: A Laboratory Manual*, (Elsevier, N.Y., 1985), the relevant disclosure of which is hereby incorporated by reference.

Various mammalian cell culture systems can be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors may comprise nontranscribed elements such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Additional details regarding the use of mammalian high expression vectors to produce a recombinant mammalian IL-7 are provided in Examples 3 and 8, below. Exemplary vectors can be constructed as disclosed by Okayama and Berg, *Mol. Cell. Biol.* 3:280 (1983), Cosman et al., *Nature* 312:768 (1984), Cosman et al., *Mol. Immunol.* 23:935 (1986), or Clark et al., U.S. Pat. No. 4,675,285.

Yeast systems, preferably employing Saccharomyces species such as *S. cerevisiae*, can also be employed for expression of the recombinant proteins of this invention, as well as yeast of other genera, for example, Pichia or Kluyveromyces.

Generally, useful yeast vectors will include origins of replication and selectable markers permitting transformation of both yeast and *E. coli*, e.g., the ampicillin resistance gene of *E. coli* and *S. cerevisiae* TRP1 gene, and a promoter derived from a highly-expressed yeast gene to induce transcription of a downstream structural sequence. Such promoters can be derived from yeast transcriptional units encoding highly expressed genes such as 3-phosphoglycerate kinase (PGK), α-factor, acid phosphatase, or heat shock proteins, among others. The heterologous structural sequence is assembled in appropriate frame with translation initiation and termination sequences, and, preferably, a leader sequence capable of directing secretion of translated protein into the extracellular medium. Optionally, the heterologous sequence can encode a fusion protein including an N-terminal identification peptide (e.g., Asp-Tyr-Lys-(Asp)$_4$-Lys) or other sequence imparting desired characteristics, e.g., stabilization or simplified purification of expressed recombinant product.

Useful yeast vectors can be assembled using DNA sequences from pBR322 for selection and replication in *E. coli* (Amp$^r$ gene and origin of replication) and yeast DNA sequences including a glucose-repressible alcohol dehydrogenase 2 (ADH2) promoter. The ADH2 promoter has been described by Russell et al., *J. Biol. Chem.* 258:2674 (1982) and Beier et al., *Nature* 300:724 (1982). Such vectors may also include a yeast TRP1 gene as a selectable marker and the yeast 2µ origin of replication. A yeast leader sequence, for example, the α-factor leader which directs secretion of heterologous proteins from a yeast host, can be inserted between the promoter and the structural gene to be expressed. See Kurjan et al., U.S. Pat. No. 4,546,082; Kurjan et al., *Cell* 30:933 (1982); and Bitter et al., *Proc. Natl. Acad. Sci. USA* 81:5330 (1984). The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929 (1978), selecting for Trp+ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification. Use of a yeast expression system to produce a recombinant mammalian IL-7 is described in Example 4, below.

Useful expression vectors for bacterial use are constructed by inserting a structural DNA sequence encoding mammalian IL-7 together with suitable translation initiation and termination signals in operable reading phase with a functional promoter. The vector will comprise one or more phenotypic selectable markers and an origin of replication to ensure amplification within the host. Suitable prokaryotic hosts for transformation include *E. coli, Bacillus subtilis, Salmonella typhimurium,* and various species within the genera Pseudomonas, Streptomyces, and Staphylococcus, although others may also be employed as a matter of choice.

Expression vectors are conveniently constructed by cleavage of cDNA clones at sites close to the codon encoding the N-terminal residue of the mature protein. For example, the murine cDNA can be cut with NdeI or ClaI, or the human cDNA with ClaI, to generate a fragment comprising substantially the entire coding region. Synthetic oligonucleotides can then be used to "add back" any deleted sections of the coding region and provide a linking sequence for ligation of the coding fragment in appropriate reading frame in the expression vector, and optionally a codon specifying an initiator methionine.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. A particularly useful bacterial expression system employs the phage λ $P_L$ promoter and cI857ts thermolabile repressor. Plasmid vectors available from the American Type Culture Collection which incorporate derivatives of the λ $P_L$ promoter include plasmid pHUB2, resident in *E. coli* strain JMB9 (ATCC 37092) and pPLc28, resident in *E. coli* RR1 (ATCC 53082). Other useful promoters for expression in *E. coli* include the T7 RNA polymerase promoter described by Studier et al., *J. Mol. Biol.* 189:113 (1986), the lacZ promoter described by Lauer, *J. Mol. Appl. Genet.* 1:139–147 (1981) and available as ATCC 37121, and the tac promoter described by Maniatis, *Molecular Cloning: A Laboratory Manual* (Cold Spring Harbor Laboratory, 1982, p 412) and available as ATCC 37138.

Following transformation of a suitable host strain and growth of the host strain to an appropriate cell density, the selected promoter is derepressed by appropriate means (e.g., temperature shift or chemical induction) and cells cultured for an additional period. Cells are typically harvested by centrifugation, disrupted by physical or chemical means, and the resulting crude extract retained for further purification. Cells are grown, for example, in a 10 liter fermenter employing conditions of maximum aeration and vigorous agitation. An antifoaming agent (Antifoam A) is preferably employed. Cultures are grown at 30° C. in the superinduction medium disclosed by Mott et al., *Proc. Natl. Acad. Sci. USA* 82:88 (1985), optionally including antibiotics, derepressed at a cell density corresponding to $A_{600}=0.4-0.5$ by elevating the temperature to 42° C., and harvested from 2–20, preferably 3–6, hours after the upward temperature shift. The cell mass is initially concentrated by filtration or other means, then centrifuged at 10,000×g for 10 minutes at 4° C. followed by rapidly freezing the cell pellet.

Use of a bacterial expression system to produce a recombinant mammalian IL-7 is described in Example 5, below.

8. Purification Processes

Preferably, purified mammalian IL-7s or bioequivalent homologues are prepared by culturing suitable host/vector systems to express the recombinant translation products of the synthetic genes of the present invention, which are then purified from culture media.

An alternative process for producing purified IL-7 involves purification from cell culture supernatants. In this approach, a cell line which elaborates useful quantities of the protein is employed. Supernatants from such cell lines can be optionally concentrated using a commercially available protein concentration filter, for example, an Amicon (trademark of W. R. Grace & Co., Danvers, Mass., USA) or Pellicon (trademark of Millipore Corp., Bedford, Mass., USA) ultrafiltration unit. Following the concentration step, the concentrate can be applied to a suitable anion exchange resin, for example, a matrix or substrate having pendant diethylaminoethyl (DEAE) groups. The matrices can be acrylamide, agarose, dextran, cellulose or other types commonly employed in protein purification. A preferred matrix is DEAE-Sephacel (Pharmacia). When media containing DEAE groups are employed, extracts containing IL-7 are applied at a weakly basic pH (e.g., pH 8) and at a sodium chloride concentration (or other suitable salt) of about 100 mM. Many contaminating proteins are bound by the ion exchanger, while IL-7 is recovered in unbound fractions.

Following anion exchange chromatography, a cation exchange step can be employed. In this step, IL-7-containing fractions are applied to a cation exchanger at weakly acid conditions with low salt (e.g., pH 5, 100 mM NaCl). IL-7 is bound by the exchanger and can be eluted in a more highly purified form at higher salt concentrations and at weakly basic pH. Suitable cation exchangers include various insoluble matrices comprising sulfopropyl or carboxymethyl groups. Sulfopropyl groups are preferred. A useful material for IL-7 purification is SP-Trisacryl (Pharmacia-LKB). Following cation exchange chromatography, an affinity step employing a matrix having a blue dye ligand has been shown to be useful. Suitable dye ligands include Blue B, which can be obtained as a conjugate with agarose (Blue B agarose). Other dye ligand equivalents can also be employed. Finally, one or more reversed-phase high performance liquid chromatography (RP-HPLC) steps employing hydrophobic RP-HPLC media, e.g., silica gel having pendant methyl or other aliphatic groups, can be employed to further purify a IL-7 composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. The protein can be renatured following bacterial expression by contact with a catalytic reducing agent at a protein concentration of 10–50 μg/ml in the presence of 1-6M guanidine HCl to prevent aggregation. Finally, high performance liquid chromatography (HPLC) can be employed for final purification steps. Microbial cells employed in expression of recombinant mammalian IL-7 can be disrupted by any convenient method, including freeze-thaw cycling, sonication, mechanical disruption, or use of cell lysing agents.

Fermentation of yeast which express mammalian IL-7 as a secreted protein greatly simplifies purification. Secreted recombinant protein resulting from a large-scale fermentation can be purified by methods analogous to those disclosed by Urdal et al., *J. Chromatog.* 296:171 (1984). This reference describes two sequential, reversed-phase HPLC steps for purification of recombinant human GM-CSF on a preparative HPLC column.

As used herein, "purified" refers to a mammalian IL-7 composition having a specific activity of at least about $10^4$ units per microgram (μg) protein in a pre-B cell proliferation assay as described elsewhere in the specification. Preferably, purified IL-7 compositions exhibit a specific activity of at least about $10^5$ units/μg.

9. Biologically Active Protein Analogs

In its various protein embodiments, the present invention provides substantially homogeneous recombinant mammalian IL-7 polypeptides free of contaminating endogenous materials and optionally, without associated native-pattern glycosylation. The native murine and human IL-7 molecules are recovered from cell culture as glycoproteins having an apparent molecular weight by SDS-PAGE of about 25 kilodaltons (kD). IL-7s expressed in mammalian expression systems, e.g., COS-7 cells, may be similar or slightly different in molecular weight and glycosylation pattern to the native molecules, depending upon the expression system. Expression of IL-7 DNAs in bacteria such as *E. coli* provides non-glycosylated molecules having an apparent molecular weight of about 16 kD by SDS-PAGE under nonreducing conditions.

Recombinant IL-7 proteins within the scope of the present invention also include N-terminal methionyl murine and human IL-7s. Additional contemplated embodiments are mammalian IL-7s expressed as fusion proteins with a polypeptide leader comprising the sequence Asp-Tyr-Lys-(Asp$_4$)-Lys, or other suitable peptide or protein sequences employed as aids to expression in microorganisms or purification of microbially-expressed proteins.

Bioequivalent and biologically active homologues or analogs of the proteins of this invention include various muteins, for example, truncated versions of IL-7s wherein terminal or internal residues or sequences not needed for biological activity are deleted, and also alloproteins such as those disclosed by Koide et al., *Proc. Natl. Acad. Sci. USA* 85:6237 (1988). As used herein, the terms "bioequivalent" and "biologically active" mean that a particular protein shares a biological activity of a native IL-7 molecule. Other muteins contemplated herein are those in which one or more cysteine residues have been deleted or replaced with other amino acids, for example, neutral amino acids, in order to provide more favorable renaturation or stability characteristics. Other approaches to mutagenesis involve modification of adjacent dibasic amino acid residues to enhance expression in yeast systems in which KEX2 protease activity is present, or modification of the protein sequence to eliminate one or more N-linked glycosylation sites. It has also been observed that deletion of residues 121-139 of the human IL-7 molecule, which have no counterparts in the murine IL-7 molecule, does not ablate biological activity in murine or human pre-B cell assay systems.

As used herein, "mutant amino acid sequence" refers to a polypeptide encoded by a nucleotide sequence intentionally made variant from a native sequence. "Mutant protein" or "mutein" means a protein comprising a mutant amino acid sequence. "Native sequence" refers to an amino acid or nucleic acid sequence which is identical to a wild-type or native form of a gene or protein. The terms "KEX2 protease recognition site" and "N-glycosylation site" are defined below. The term "inactivate," as used in defining particular aspects of the present invention, means to alter a selected KEX2 protease recognition site to retard or prevent cleavage by the KEX2 protease of *Saccharomyces cerevisiae*, or to alter an N-glycosylation site to preclude covalent bonding of oligosaccharide moieties to particular amino acid residues.

Site-specific mutagenesis procedures can be employed to inactivate KEX2 protease processing sites by deleting, adding, or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The resulting muteins are less susceptible to cleavage by the KEX2 protease at locations other than the yeast α-factor leader sequence, where cleavage upon secretion is intended.

Many secreted proteins acquire covalently attached carbohydrate units following translation, frequently in the form of oligosaccharide units linked to asparagine side chains by N-glycosidic bonds. Both the structure and number of oligosaccharide units attached to a particular secreted protein can be highly variable, resulting in a wide range of apparent molecular masses attributable to a single glycoprotein. mIL-7 and hIL-7 are secreted glycoproteins of this type. Attempts to express glycoproteins in recombinant systems can be complicated by the heterogeneity attributable to this variable carbohydrate component. For example, purified mixtures of recombinant glycoproteins such as human or murine granulocyte-macrophage colony stimulating factor (GM-CSF) can consist of from 0 to 50% carbohydrate by weight. Miyajima et al., *EMBO Journal* 5:1193 (1986) reported expression of a recombinant murine GM-CSF in which N-glycosylation sites had been mutated to preclude glycosylation and reduce heterogeneity of the yeast-expressed product.

The presence of variable quantities of associated carbohydrate in recombinant secreted glycoproteins complicates purification procedures, thereby reducing yield. In addition, should the glycoprotein be employed as a therapeutic agent, a possibility exists that recipients will develop allergic reactions to the yeast carbohydrate moieties, requiring therapy to be discontinued. For these reasons, biologically active, homogeneous analogs of immunoregulatory glycoproteins having reduced carbohydrate may be desirable for therapeutic use.

Functional mutant analogs of mammalian IL-7s having inactivated N-glycosylation sites can be produced by oligonucleotide synthesis and ligation or by site-specific mutagenesis techniques as described below. These analog proteins can be produced in a homogeneous, reduced-carbohydrate form in good yield using yeast expression systems. N-glycosylation sites in eukaryotic proteins are characterized by the amino acid triplet Asn-$A^1$-Z, where $A^1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A^1$ and Z, or an amino acid other than Asn between Asn and $A^1$. Preferably, substitutions are made conservatively; i.e., the most preferred substitute amino acids are those having physicochemical characteristics resembling those of the residue to be replaced. Similarly, when a deletion or insertion strategy is adopted, the potential effect of the deletion or insertion upon biological activity should be considered.

In addition to the particular muteins described above, numerous DNA constructions including all or part of the nucleotide sequences depicted in FIGS. 1-5, in conjunction with oligonucleotide cassettes comprising additional useful restriction sites, can be prepared as a matter of convenience. Mutations can be introduced at particular loci by synthesizing oligonucleotides containing a mutant sequence, flanked by restriction sites enabling ligation to fragments of the native sequence. Following ligation, the resulting reconstructed sequence encodes a mutein having the desired amino acid insertion, substitution, or deletion.

Alternatively, oligonucleotide-directed site-specific mutagenesis procedures can be employed to provide an altered gene having particular codons altered according to the substitution, deletion, or insertion required. Walder et al., *Gene* 42:133 (1986); Bauer et al., *Gene* 37:73 (1985); Craik, *Biotechniques*, January 1985, 12-19; Smith et al., *Genetic Engineering: Principles and Methods* (Plenum Press, 1981); and U.S. Pat. No. 4,518,584 disclose suitable techniques, and are incorporated by reference herein.

In one embodiment of the present invention, the amino acid sequence of IL-7 is linked to a yeast α-factor leader sequence via an N-terminal fusion construct comprising a nucleotide encoding the peptide Asp-Tyr-Lys-Asp-Asp-Asp-Asp-Lys (DYKDDDDK). The latter sequence is highly antigenic and provides an epitope reversibly bound by specific monoclonal antibody, enabling rapid assay and facile purification of expressed recombinant protein. This sequence is also specifically cleaved by bovine mucosal enterokinase at the residue immediately following the Asp-Lys pairing. Fusion proteins capped with this peptide may also be resistant to intracellular degradation in *E. coli*. An alternative construction is Asp-Tyr-Lys-Asp-Asp-Asp-Asp-Lys-Glu-Ile-Gly-Arg-Pro, which provides a Factor X recognition site immediately downstream from the enterokinase site.

10. Administration of IL-7

In composition and method-of-use aspects, the present invention provides therapeutic compositions comprising an effective amount of any of the mammalian IL-7 proteins of the invention and a suitable diluent or carrier, and methods for stimulating B and/or T lymphocyte development or proliferation or modulating or augmenting immune, lymphopoietic, or hematopoietic response in mammals, including humans, comprising administering an effective amount of any of the foregoing compositions. Use in conjunction or admixture with other lymphokines, e.g., IL-1α, IL-1β, IL-2, IL-3, IL-4, IL-5, IL-6, CSF-1, GM-CSF, or G-CSF, IFN-α, IFN-β or IFN-γ is also contemplated.

For therapeutic use, a purified IL-7 is administered to a mammal for treatment in a manner appropriate to the indication. Thus, for example, a mammalian IL-7 composition administered as a stimulator of pre-B or pre-T cell proliferation or modulator of immune or hematopoietic effector cell development, proliferation or function can be given by bolus injection, continuous infusion, sustained release from implants, or other suitable technique. Typically, an IL-7 therapeutic will be administered in the form of a composition comprising purified protein in conjunction with physiologically acceptable carriers, excipients or diluents. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials; generally, dosages of 10 ng to 100 μg/kg/day, preferably 100 ng to 1 μg/kg/day for 1-20 days, can be expected to induce a biological effect. For example, bolus injections of 1 μg/kg can be given at 4-day intervals as a stimulator of hematopoietic cell development.

The following examples illustrate particular aspects of the present invention, including purification of native murine IL-7, cloning and expression of genes encoding murine and human IL-7 proteins, purification of recombinant murine and human IL-7 proteins to homogeneity, biological assays involving use of purified IL-7 proteins, and administration of purified IL-7 proteins to mammals in a model therapeutic regime. In the examples, all procedures involving use of DNA enzymes, for example, restriction endonucleases and DNA polymerases, were conducted according to the instructions provided by the manufacturer. All probes were labelled with $^{32}P$. Other standard nucleic acid manipulation technologies are substantially similar to those disclosed by Maniatis, supra, and by Ausubel et al, eds., *Current Protocols in Molecular Biology* (Wiley-Interscience, Media, Pa., USA).

EXAMPLE 1

Creation of a Murine IL-7 Producing Cell Line (I×N/A6) by Transfection; Purification of Murine IL-7 from Cell Supernatants Adherent bone marrow stromal cells were transfected with the plasmid pSV3neo containing the SV40 T antigen transforming sequences using a calcium phosphate procedure as described by Southern et al., *J. Mol. Appl. Genet.* 1:327 (1982), and Graham et al., *Virology* 52:456 (1973); as modified by Wigler et al., *Cell* 14:725 (1978). The transfected adherent cells were removed with trypsin:EDTA and cloned by limiting dilution. The supernatants from the resultant clones were tested for IL-7 activity and the best producer (I×N/A6) was expanded for further study. This cell line was monitored on a monthly basis for mycoplasma using commercially-available mycoplasma detection kits.

Conditioned media from I×N/A6 cells was generated in 1750 cm$^2$ tissue culture roller bottles (Falcon #3029) in the following manner. When the cells reached confluence the medium was replaced with 1 liter/roller bottle of serum-free RPMI supplemented with 2.3 gm/liter glucose and 1.54 gm/liter of sodium bicarbonate and containing as a stimulant 1 μg/ml S. typhimurium LPS. The bottles were gassed with 10% $CO_2$ in air and incubated for six days. The supernatant was harvested and then concentrated 20 fold in an Amicon DC10 hollow fiber apparatus (10,000 MW cut off). The crude concentrates were sterilized by filtration before assay and purification.

One liter of the crude concentrated conditioned medium was adjusted to pH 8 with 1N NaOH and diluted with sterile distilled water to a conductivity of 1 m Siemen/cm (a conductivity of 1 m Siemen/cm corresponds to a sodium chloride concentration of 100 mM on a Radiometer CDM83 conductivity meter). The concentrate was then applied to a DEAE-Sephacel (Pharmacia) column (5.0×15 cm) previously equilibrated with 20 mM Tris-HCl (pH 8) containing 100 mM NaCl. The effluent was monitored by $OD_{280}$ and the protein containing flow-through fraction was collected for further purification.

The non-binding fraction from the DEAE-Sephacel column was adjusted to pH 5 with 1M citric acid (free acid). This was then applied directly to a column (3.2×12.5 cm) of SP-Trisacryl (Pharmacia-LKB) which had previously been equilibrated in 10 mM citrate (pH 5.0) containing 100 mM NaCl. The column was washed with five column volumes of equilibration buffer followed by washing with five column volumes of 20 mM Tris-HCl (pH 8). When the pH of the column effluent reached pH 8 and the $OD_{280}$ had returned to baseline values the column was eluted with a one liter linear gradient from 0.0 to 0.5M sodium chloride in 20 mM Tris-HCl (pH 8). The elution was carried out at a flow rate of 50 ml/hr and 10 ml fractions were collected and assayed for the presence of IL-7.

Pooled IL-7-containing fractions from two separate SP-Trisacryl elutions were pooled and applied directly to a column (2.5×40 cm) of Blue B agarose (Amicon Corp., Danvers, Mass., USA) which had previously been equilibrated in 20 mM Tris-HCl (pH 8) containing 125 mM NaCl. The sample was applied at a flow rate of 15 ml/hr. After washing with equilibration buffer until the $OD_{280}$ had returned to baseline values, the column was eluted with a one liter linear gradient from 0.125 to 2M NaCl in 20 mM Tris-HCl (pH 8). Ten ml fractions were collected at a flow rate of 25 ml/hr and assayed for IL-7 activity.

High performance liquid chromatography (HPLC) was performed with a Waters Associates (Milford, Mass.) liquid chromatograph equipped with two model 510 pumps, a model 720 system controller, and a model 441 absorbance detector monitoring at 214 nm essentially as described by Urdal et al., J. Chrom. 296:171 (1984). Large sample volumes were pumped onto columns with a minipump.

Fractions containing IL-7 activity from the Blue B agarose chromatographic step were applied at a flow rate of 5 ml/min to an 8 mm×10 cm radial PAK cartridge (Waters Associates) containing 15-20μ Vydac C-4 reversed phase silica (Separations Group, Hesperia, Calif., USA). Water containing 0.1% trifluoroacetic-acid (TFA, solvent A) was flushed through the columns until the absorbance at 214 nm was down to baseline levels. At this time a linear gradient was established leading from 0 to 100% solvent B (acetonitrile containing 0.1% TFA) at a rate of 1% solvent B/min and a flow rate of 1 ml/minute.

Active fractions following a single HPLC phase were pooled, diluted with two volumes of 0.9M acetic acid and 0.2M pyridine (pH 4.0, Buffer $A_2$) and applied to the same column after re-equilibration in the pyridine-acetate solvent system. A gradient of solvent $B_2$ (0.9M acetic acid, 0.2M pyridine, and 60% N-propanol) was then applied to the column, leading from 0 to 20% solvent $B_2$ in 10 minutes, and from 20% $B_2$ to 84% $B_2$ in 100 minutes, at a flow rate of 1 ml/min.

Fractions containing activity from this second HPLC phase were pooled, diluted with two volumes of solvent $A_2$, and applied to a 3.9 mm by 30 cm radial PAK column packed with 10μ Vydac C-18 reversed phase silica that had been previously equilibrated in 20% solvent $B_2$. A gradient of solvent $B_2$ from 20% to 84% was used to elute protein from the column. Fractions containing activity from the third phase of HPLC were diluted with two volumes of solvent $A_1$ (0.1% TFA) and applied to the C-18 column previously equilibrated in 20% solvent $B_1$ (acetonitrile, 0.1% TFA) and a gradient of solvent $B_1$ established from 20% to 100% $B_1$ at a rate of change of 1% per minute and a flow rate of 1 ml/min was used to elute IL-7.

SDS-PAGE was performed by a modification of the method described by Laemmli, Nature 227:680 (1970). Material purified through four phases of RP-HPLC was evaporated to dryness under vacuum in a lyophilizer and redissolved in a small volume of SDS sample buffer without 2-mercaptoethanol. The sample was electrophoresed onto a 12% polyacrylamide gel. The appropriate lane of the resulting gel was sliced into 1-2 mm sections, and each section minced and eluted by diffusion overnight into 0.2% SDS; the biological activity in each fraction was then determined. The active fractions were pooled and an aliquot analyzed following electrophoresis on a Phastgel PAGE System (Pharmacia) utilizing a 10-15% gradient gel. Proteins were visualized using a silver staining method.

Table 1, below, summarizes the results of the procedures used to purify IL-7. At pH 8.0 and 100 mM NaCl, the IL-7 activity in the concentrated medium from I×N/A6 cells did not bind to the DEAE Sephacel column, although ninety percent of the total protein present in the crude conditioned medium, including that responsible for macrophage colony stimulating activity, did bind to the column. Subsequent chromatography steps, including SP-Trisacryl, Blue B agarose, and four separate reversed phase HPLC protocols resulted in a 200,000 fold purification of IL-7 activity.

TABLE 1

Purification of Murine Interleukin-7 (IL-7)

| Step | S.A. (units/μg) | Purification (-fold) | Yield % |
|---|---|---|---|
| 1. Concentrate | 0.38 | 1 | — |
| 2. DEAE-Sephacel (unbd.) | 4.63 | 12.2 | 100 |
| 3. SP-Trisacryl | 153 | 403 | 113 |
| 4. Blue B Agarose | 423 | 1113 | 80 |
| 5. RP-HPLC | $8 \times 10^4$ | $2 \times 10^5$ | 50 |

TABLE 1-continued

Purification of Murine Interleukin-7 (IL-7)

| Step | S.A. (units/µg) | Purification (-fold) | Yield % |
|---|---|---|---|
| 6. SDS-PAGE | $4 \times 10^6$ | $10 \times 10^6$ | 35 |

Processing 800 liters of crude conditioned medium in this fashion resulted in four HPLC column fractions which contained a total of $5 \times 10^6$ units of IL-7 activity. Analysis of this material by SDS-PAGE and silver staining or $^{125}$I labeling revealed that a number of proteins were still present at this stage of purification. The major protein present in this material exhibited a mass of 18,000; however, faint bands above and below this band were detectable.

Two experiments were performed in order to identify the protein in this mixture that was responsible for IL-7 activity. In the first, IL-7 was applied to SDS-PAGE under nonreducing conditions. Following completion of electrophoresis, the gel was cut into 1 mm bands and the protein in each band was eluted into media and assayed for biological activity. The results indicated that IL-7 biological activity was associated with a protein of $M_r$ 25,000 and was distinct from the region of the gel corresponding to that containing the $M_r$ 18,000 protein band. No activity was isolated when electrophoresis was performed under reducing conditions.

In the second experiment, $^{125}$I-labeled IL-7 was absorbed to cells that respond to this factor (IxN/2b). IxN/2b is a clonal cell line derived from the non-adherent pre-B cells from a long term bone marrow culture. These cells can be grown in the absence of exogenous feeder cells and are strictly dependent upon purified IL-7 for continued growth and viability. The cells were washed and then extracted with PBS containing 1% Triton X-100 (polyoxyethylene ether surfactant, Rohm & Huss Co., Philadelphia, Pa., USA). An aliquot of this material was then analyzed following SDS-PAGE by autoradiography. The results showed that only a protein of $M_r$ 25,000 appeared to bind to IL-7 responsive cells. Excess unlabeled IL-7 inhibited binding of this protein, and control cells that do not respond to IL-7 failed to bind the $M_r$ 25,000 protein. The results of both experiments suggested that a protein of $M_r$ 25,000 was responsible for IL-7 activity.

The resistance of IL-7 activity to SDS-PAGE suggested that this procedure could be used as the final step in the purification of this protein. The results showed that as found in the pilot experiment, IL-7 activity eluted at a position coinciding with a protein of $M_r$ 25,000. PAGE analysis of this bioactive fraction revealed a single protein detected by silver staining. Protein sequencing by Edman degradation using an Applied Biosystems (Foster City, Calif., USA) automated sequencer indicated the following N-terminal amino acid sequence: X-X-His-Ile-Lys-Asp-Lys-Glu-X-Lys-Ala-Tyr-Glu-X-Val-Met.

The final specific activity was preliminarily estimated to be $4 \times 10^6$ units/µg protein which would represent a purification of 10 million fold from the starting material. For the reasons noted previously, this estimate has been revised downward to approximately $2 \times 10^5$ units/µg, equivalent to the specific activity of homogeneous recombinant murine IL-7 produced in COS-7 cells.

EXAMPLE 2

Isolation of cDNA Encoding Murine IL-7 by Direct Expression of Active Protein in COS-7 Cells A cDNA library was constructed by reverse transcription of polyadenylated mRNA isolated from total RNA extracted from IxN/A6 cells grown under IL-7-inducing conditions. The cells were cultured in RPMI 1640 medium plus 5% fetal bovine serum for 48 hours in the presence of 10 ng/ml phorbol myristyl acetate (PMA) and 1 µg/ml S. typhimurium LPS to elicit maximal IL-7 specific messenger RNA production. Cells were harvested using trypsin-EDTA and cytoplasmic RNA isolated using an NP40 lysis procedure substantially similar to that disclosed by Pennica et al., Nature 301:214 (1983). Poly A+ RNA was isolated by oligo dT cellulose chromatography and double-stranded cDNA was prepared using reverse transcriptase. The blunt-ended cDNA was ligated into SmaI-cut dephosphorylated pDC201 vector DNA.

The eukaryotic high expression vector pDC201 (see Example 7 and FIG. 7) was assembled from SV40, adenovirus 2, and pBR322 DNA comprising, in sequence: (1) and SV40 fragment containing the origin of replication, early and late promoters, and enhancer; (2) an adenovirus 2 fragment containing the major late promoter, the first exon and part of the first intron of the tripartite late leader; (3) a synthetic sequence comprising a HindIII site, a splice acceptor site, the second and third exons of the adenovirus 2 tripartite leader and a multiple cloning site including a SmaI site; (4) additional SV40 sequences containing early and late polyadenylation sites; (5) adenovirus 2 sequences including the virus-associated RNA genes; and (6) pBR322 elements for replication in E. coli.

The resulting IxN/A6 cDNA library in pDC201 was used to transform E. coli strain DH5α, and recombinants were plated to provide approximately 1000 colonies per plate and sufficient plates to provide approximately 50,000 total colonies per screen. Colonies were scraped from each plate, pooled, and plasmid DNA prepared from each pool. The pooled DNA was then used to transfect a sub-confluent layer of monkey COS-7 cells using DEAE-dextran followed by chloroquine treatment, as described by Luthman et al., Nucleic Acids Res. 11:1295 (1983) and McCutchan et al., J. Natl. Cancer Inst. 41:351 (1968). The cells were then grown in culture for three days to permit transient expression of the inserted sequences. After three days, cell culture supernatants were assayed for IL-7 activity using the pre-B cell proliferation assay as described elsewhere in the specification. After approximately 720,000 recombinants from the library had been screened in this manner, one transfectant pool was observed to elaborate IL-7 activity in the proliferation assay at a level tenfold above background.

A frozen stock of bacteria from the positive pool was then used to obtain plates of approximately 200 colonies. These plates were treated as before to obtain plasmid DNA from the pooled bacterial colonies, and the DNA was transfected into COS-7 cells as described above. Following identification of a positive pool, plasmid DNA was prepared from individual colonies and again screened by COS-7 cell transfection. In this manner, a single clone was isolated which was capable of inducing expression of IL-7 in COS-7 cells. The insert was subcloned and sequenced by conventional techniques. The sequence is set forth in FIG. 2.

EXAMPLE 3

Isolation of cDNA Encoding Human IL-7 and Expression of Active Protein in COS-7 Cells Initial attempts to detect human IL-7 mRNA on Northern blots using nick-translated murine IL-7 cDNA were unsuccessful. However, it was possible to obtain hybridization of the murine probe to Southern blots of human genomic DNA. Thus, a search for a human IL-7 cDNA was initiated by first screening a commercially-available human genomic library. Approximately 400,000 human genomic clones were screened with nick-translated murine IL-7 cDNA using the techniques described by Benton and Davis, Science 196:180 (1977). This screen yielded a single hybridizing clone which was purified and restriction mapped. Southern blots of this cloned genomic DNA indicated that the hybridization to the murine probe was limited to a 1.2 kb EcoRI fragment. This fragment was subcloned and sequenced, revealing that it corresponded to the 5' noncoding region of the gene, extending to the first 10 bases of the coding region, whereupon the human genomic DNA sequence diverged from the murine IL-7 cDNA sequence due to the presence of an intron. The determination of this genomic sequence enabled synthesis of oligonucleotides having sequences complementary to the human IL-7 RNA transcript. Two such oligonucleotides of 29 and 31 bases were synthesized, labeled with $^{32}P$ using T4 polynucleotide kinase, and used to probe Northern blots of RNA from a number of human cell lines. These probes were found to specifically hybridize to two size classes of mRNA from a human liver adenocarcinoma cell line, SK-HEP-1 (ATCC HTB 52).

A cDNA library was constructed by reverse transcription of polyadenylated mRNA isolated from total RNA extracted from SK-HEP-1. The cells were cultured in RPMI 1640 medium plus 10% fetal bovine serum for 16 hours in the presence of 1 µg/ml LPS to elicit hIL-7 mRNA synthesis. Polyadenylated mRNA was isolated by chromatography on oligo-dT cellulose, and reverse transcribed using standard techniques to provide a first strand cDNA. This cDNA was rendered double-stranded using DNA polymerase I, blunt-ended with T4 DNA polymerase, methylated with EcoRI methylase to protect EcoRI cleavage sites within the cDNA, and ligated to EcoRI linkers. The resulting constructs were digested with EcoRI to remove all but one copy of the linkers at each end of the cDNA, and ligated to EcoRI-cut and dephosphorylated arms of bacteriophage λgt10 (Huynh et al., DNA Cloning: A Practical Approach, Glover, ed., IRL Press, pp. 49–78). The ligated DNA was packaged into phage particles using a commercially available kit to generate a library of recombinants (Stratagene Cloning Systems, San Diego, Calif., USA). Recombinants were plated on E. coli strain C600(hfl−) and screened by standard plaque hybridization techniques under conditions of moderate stringency (50° C., 0.9M NaCl) using the same kinased oligonucleotides which hybridized to the mRNA. In screening approximately 150,000 plaques, one clone was isolated from the library which hybridized to the probes when the filters were washed with 1×SSC at 55° C. This clone (hIL-7 cDNA #1) was plaque purified and the insert DNA purified and subcloned into an EcoRI-cut derivative (pGEMBL18) of the standard cloning vector pBR322 containing a polylinker having a unique EcoRI site, a BamH1 site and numerous other unique restriction sites. An exemplary vector of this type is described by Dente et al., Nucleic Acids Research 11:1645 (1983).

This cDNA was then sequenced and shown to be 1465 base pairs in length, with an open reading frame able to code for a protein of 133 amino acids. Both the DNA and amino acid sequence of this human cDNA showed approximately 78% homology with the murine IL-7 cDNA. However, when this human cDNA was subcloned into the SmaI site of pDC201 to enable its expression in COS-7 cells, no IL-7 activity was detected in the culture supernatants following transfection.

In order to obtain additional human IL-7 cDNAs, approximately one million λgt10 bacteriophage containing cDNAs derived from SK-HEP-1 poly A+ RNA were screened using nick-translated human IL-7 cDNA #1. This resulted in the isolation of 5 additional cDNAs which were then inserted into the SmaI site of pDC201. These constructs were then transfected into COS-7 cells and the culture supernatants assayed for IL-7 activity. One cDNA, designated hIL-7 #3, exhibited detectable IL-7 activity. This cDNA was subcloned into pGEMBL18 and sequenced. The cDNA sequence is shown in FIG. 4; the coding sequence and deduced amino acid sequence of hIL-7 are shown in FIG. 5.

EXAMPLE 4

Expression of Murine IL-7 in a Yeast System

To create a yeast expression vector for mIL-7, yeast plasmid pBC10, which is a derivative and equivalent of pYαHuGM (ATCC 53157) was altered as follows. pBC10 is a yeast/bacterial shuttle vector comprising (1) an origin of replication and Amp$^r$ gene from pBR322 enabling selection and replication in E. coli; (2) the TRP1 gene and 2µ origin of replication for selection and replication in S. cerevisiae; (3) the yeast alcohol dehydrogenase 2 (ADH2) promoter followed by the yeast pre-pro α-factor leader sequence to allow foreign protein expression and secretion from yeast; and (4) a multiple cloning site including a SpeI site. pBC10 was digested to completion with Asp718 and SpeI, the vector fragment isolated and ligated to the following oligonucleotide A, which provides an N-terminal epitope or identification leader Asp-Tyr-Lys-(Asp$_4$)-Lys ("flag") fused adjacent to and in-frame with the α-factor leader sequence, followed by a Factor X protease recognition site, and a polylinker sequence comprising StuI, NcoI, BamH1, SmaI and SpeI cleavage sites:

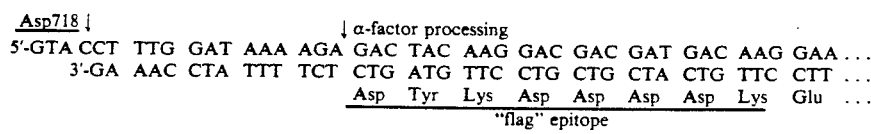

```
       Asp718 ↓                    ↓ α-factor processing
5'-GTA CCT TTG GAT AAA AGA GAC TAC AAG GAC GAC GAT GAC AAG GAA ...
3'-GA  AAC CTA TTT TCT CTG ATG TTC CTG CTG CTA CTG TTC CTT ...
                         Asp Tyr Lys Asp Asp Asp Asp Lys Glu ...
                                    "flag" epitope
```

```
                ↓ StuI    ↓ NcoI              ↓ SmaI    ↓ SpeI
    ...ATC GAA GGT AGG CCT CCA TGG ATC CCC CGG GAC A-3'
    ...TAG CTT CCA TCC GGA GGT ACC TAG GGG GCC CTG TGA TC-5'
    ...Ile Glu Gly Arg Pro         ↑ BamH1
       Factor X site                           polylinker
```

The resulting construct, designated pIXY166, was then digested with StuI and SpeI, and the vector ligated to a ~950 bp NdeI-XbaI fragment including the majority of the coding region of the mIL-7 cDNA, and the following oligonucleotide linker, which adds back the N-terminal 11 amino acids of the mature sequence of mIL-7 up to the internal NdeI site:

an 85 amino acid signal peptide derived from the gene encoding the secreted peptide α-factor (See Kurjan et al., U.S. Pat. No. 4,546,082). An Asp718 restriction site was introduced at position 237 in the α-factor signal peptide to facilitate fusion to heterologous genes. This was achieved by changing the thymidine residue at nucleotide 241 to a cytosine residue by oligonucleotide-

```
5'-GAG TGC CAC ATT AAA GAC AAA GAA GGT AAA GCA-3'
3'-CTC ACG GTG TAA TTT CTG TTT CTT CCA TTT CGT AT-5'
   Glu Cys His Ile Lys Asp Lys Glu Gly Lys Ala
```

This expression vector, designated pIXY171, was purified and employed to transform a diploid yeast strain of S. cerevisiae (XV2181) by standard techniques, such as those disclosed in EPA 0165654, selecting for tryptophan prototrophs. The resulting transformants were cultured for expression of a flag-mIL-7 fusion protein.

directed in vitro mutagenesis as described by Craik, Biotechniques, January 1985, 12-19. A synthetic oligonucleotide containing multiple cloning sites and having the following sequence was inserted from the Asp718 site at amino acid 79 near the 3' end of the α-factor signal peptide to a SpeI site in the 2μ sequence:

```
Asp718                                         StuI    NcoI    BamHI
GTACCTTTGGATAAAAGAGACTACAAGGACGACGATGACAAGAGGCCTCCATGGAT...
      GAAACCTATTTTCTCTGATGTTCCTGCTGCTACTGTTCTCCGGAGGTACCTA...
                                                    |←———— Polylinker ————

SmaI          SpeI
    ...CCCCCGGGACA
    ...GGGGGCCCTGTGATC
    ———— Polylinker ————→|
```

Cultures to be assayed for biological activity were grown in 20-50 ml of YPD medium (1% yeast extract, 2% peptone, 1% glucose) at 37° C. to a cell density of 1-5×10⁸ cells/ml. Cells were then removed by centrifugation and the medium was filtered through a 0.45μ cellulose acetate filter. Supernatants produced by the transformed yeast strain were then assayed by reaction with a mouse monoclonal antibody followed by horseradish peroxidase conjugated goat anti-mouse antibody to detect the presence of the flag peptide, and also assayed by the pre-B cell proliferation assay for IL-7 activity, which confirmed expression of a biologically active protein.

EXAMPLE 5

Expression of Human IL-7 in Yeast

For expression of hIL-7, a yeast expression vector derived from pIXY120 is constructed as follows. pIXY120 is identical to pYαHuGM (ATCC 53157), except that it contains no cDNA insert and includes a polylinker/multiple cloning site with an NcoI site. This vector includes DNA sequences from the following sources: (1) a large SphI (nucleotide 562) to EcoRI (nucleotide 4361) fragment excised from plasmid pBR322 (ATCC 37017), including the origin of replication and the ampicillin resistance marker for selection in E. coli; (2) S. cerevisiae DNA including the TRP-1 marker, 2μ origin of replication, ADH2 promoter; and (3) DNA encoding pBC120 also varies from pYαHuGM by the presence of a 514 bp DNA fragment derived from the single-standed phage f1 containing the origin of replication and intergenic region, which has been inserted at the NruI site in the pBR322 sequence. The presence of an f1 origin of replication permits generation of single-stranded DNA copies of the vector when transformed into appropriate strains of E. coli and superinfected with bacteriophage f1, which facilitates DNA sequencing of the vector and provides a basis for in vitro mutagenesis. To insert a cDNA, pIXY120 is digested with Asp718 which cleaves near the 3' end of the α-factor leader peptide (nucleotide 237) and, for example, NcoI which cleaves in the polylinker. The large vector fragment is then purified and ligated to a DNA fragment encoding the protein to be expressed.

To create a secretion vector for expressing human IL-7, a cDNA fragment encoding hIL-7 from the ClaI site (see FIG. 1) to an NcoI site located 3' to the open reading frame is excised from a cDNA containing the complete hIL-7 sequence. pIXY120 is digested with Asp718 near the 3' end of the α-factor leader and NcoI. The vector fragment is ligated to the ClaI-NcoI hIL-7 cDNA fragment and the following oligonucleotide, which regenerates the last five amino acids of the α-factor leader and the first 20 amino acids of mature hIL-7.

```
α-factor processing ─────────── ↓           EcoRV
GTA CCT TTG GAT AAA AGA GAT TGT GAT ATC GAA GGT AAA GAT GGC ...
    GA AAC CTA TTT TCT CTA ACA CTA TAG CTT CCA TTT CTA CCG ...
    Pro Leu Asp Lys Arg Asp Cys Asp Ile Glu Gly Lys Asp Gly ...
                         | ←——— hIL-7 ———→

... AAA CAA TAT GAG AGT GTT CTA ATG GTC AGC AT
... TTT CTT ATA CTC TCA CAA GAT TAC CAG TCG TAG C
    Lys Gln Tyr Glu Ser Val Leu Met Val Ser Ile
```

The oligonucleotide also includes a T→C change at nucleotide 12 to introduce an EcoRV restriction site, without altering the encoded amino acid sequence. The resulting hIL-7 expression vector is designated pIXY192.

To create an intracellular expression vector for hIL-7 production in *S. cerevisiae*, pIXY120 is digested with XhoI (which cleaves 5' to the α-factor leader sequence) and NcoI to remove the DNA sequence encoding the leader. The vector fragment is isolated and ligated to an EcoRV-NcoI fragment encoding hIL-7 from nucleotide 12, derived from pIXY192 (as described above) and the following oligonucleotide:

```
T CGA GAC AAA ATG GAT TGT GA
  CTG TTT TAC CTA ACA CT
          Met Asp Cys Asp
```

This oligonucleotide joins mature hIL-7 to the yeast ADH2 promoter and provides an initiator methionine codon and the first three amino acids of mature hIL-7 up to the EcoRV site. The resulting vector is designated pIXY193.

The foregoing expression vectors are then purified and employed to transform a diploid yeast strain of *S. cerevisiae* (XV2181) by standard techniques, such as those disclosed in EPA 165,654, selecting for tryptophan prototrophs. The resulting transformants are cultured for expression of an hIL-7 protein either intracellularly or as a secreted protein. Cultures to be assayed for biological activity are grown in 20–50 ml of YPD medium (1% yeast extract, 2% peptone, 1% glucose) at 37° C. to a cell density of $1–5 \times 10^8$ cells/ml. To separate cells from medium, cells are removed by centrifugation and the medium filtered through a 0.45μ cellulose acetate filter prior to assay. Supernatants produced by the pIXY192-transformed yeast strain, or crude extracts prepared from disrupted yeast cells transformed by pIXY193, are assayed using the pre-B cell proliferation assay for IL-7 activity to verify expression of a biologically active protein.

EXAMPLE 6

Expression of Murine IL-7 in *E. coli*

Mature mIL-7 was expressed intracellularly in *E. coli* by placing the coding region downstream of the bacteriophage λ leftward promoter $P_L$. The mRNA produced by the plasmid contains a consensus ribosome binding site and ATG (initiator methionine codon). The expression plasmid was constructed as follows. First, plasmid pLNbIL2 (ATCC 53202; see EPA 215,576) was digested with XbaI and StuI, and the resulting 5.2 kb vector fragment was recovered. Second, a synthetic oligonucleotide was synthesized to link the transcriptional unit of the truncated N gene of phage lambda to a consensus ribosome binding site (cRBS) and coding region of mIL-7 up to the NdeI site (See FIG. 1). This oligonucleotide had the following sequence:

```
(XbaI)   BglII            cRBS
CTAGATCTCT AAGGAGGTAAAAAAAT ATG GAA TGT CAT ATT AAA GAT AAA GAA GGT ...
 TAGAGA TTCCTCCATTTTTTTA  TAC CTT ACA GTA TAA TTT CTA TTT CTT CCA ...
                              Met Glu Cys His Ile Lys Asp Lys Glu Gly ...

(NdeI)
         ... AAA GCA
         ... TTT CGTAT
         ... Lys Ala
```

Third, a restriction fragment containing the majority of the mIL-7 coding region was recovered from the clone isolated as described in Example 2 by NdeI and PvuII digestion. The foregoing three fragments were ligated together to provide an expression plasmid designated pLNPBGF. This plasmid was used to transform *E. coli* strain K802:pRK248cIts (ATCC 33526; ATCC 33766), which was then cultured in super induction medium [See Mott et al., *Proc. Natl. Acad. Sci. USA* 82:88 (1985)]. Expression of the recombinant transcriptional unit was induced by shifting culture temperature from 30° C. to 42° C. when cultures reached an $OD_{600}$ of about 0.5, and then held at that temperature for approximately two hours. At this point, cells were harvested and the resulting cell pellet dissolved in an extraction buffer consisting of (for pellet corresponding to 1 ml culture) 0.5 ml 7M guanidine HCl, 10 mM citrate pH 7.0, 5 mM EDTA, 0.1% beta mercaptoethanol and 0.1% Triton X100. The resulting fully denatured cell extract was then rapidly diluted (1 part per 100) in tissue culture medium (RPMI 1640) containing 1% bovine serum albumin. This procedure resulted in expression of 20–50,000 units of activity per ml of cell extract.

The level of mIL-7 expression was improved approximately 100 fold by transferring a restriction fragment from pLNPBGF encoding the protein into a plasmid containing a shortened 5' noncoding region. This expression plasmid (designated pPL1ppPBGF) was constructed from plasmid pPL3 as follows. pPL3 is a derivative of the commercially available plasmid pGEM1 (Promega Biotec, Madison, Wis., USA) containing a temperature sensitive λ $P_L$ promoter substantially similar to that described in detail by Gourse et al., *Proc. Natl. Acad. Sci. USA* 82:1069 (1985). Similar λ $P_L$ promoter sequences are present on the plasmids pHUB2, resident in *E. coli* strain JMB9 (ATCC 37092) and pPLc28, resident in *E. coli* RR1 (ATCC 53082). pPL3 was digested with HindIII, the resulting linearized plasmid blunt-ended with T4 polymerase, and then digested with Asp718. A synthetic oligonucleotide was then prepared having the following sequence:

```
(Asp718)                            (XbaI)
GTACCGCTACATGGAGATTAACTCAAT
   GCGATGTACCTCTAATTGTGTTAGATC.
```

A restriction fragment from pLNPBGF containing the entire coding region was generated by digestion with XbaI and SspI. The foregoing elements were ligated together using standard techniques and the resulting plasmid pPLlppPBGF used to transform K802:pRK248cIts. When this strain was induced as described above, approximately 2.5–3.2 million units of pre-B cell growth promoting activity were generated per ml of culture medium in cell extracts prepared as described above. In addition, SDS-PAGE indicated a densely staining protein band in a position consistent with the molecular weight of mature mIL-7.

EXAMPLE 7

Figure 7:
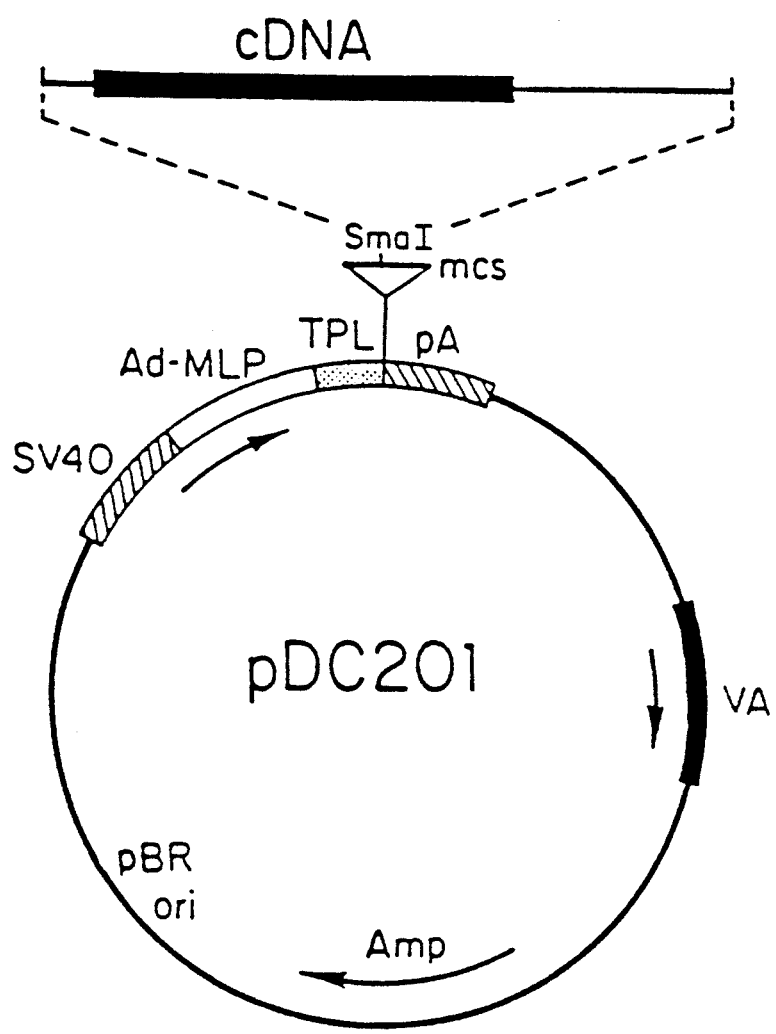
FIG. 7 is a schematic illustration of the mammalian high expression plasmid pDC201, which is described in greater detail in Example 7.

Expression of Recombinant Human IL-7 Using High-Efficiency Mammalian Expression Systems The mammalian expression plasmid pDC201, depicted in FIG. 7, is designed to express cDNA sequences inserted at its multiple cloning site (MCS) when transfected into mammalian cells. Referring now to FIG. 7, pDC201 includes the following components: SV40 (hatched box) contains SV40 sequences from coordinates 5171-270 including the origin of replication, enhancer sequences and early and late promoters. The fragment is oriented so that the direction of transcription from the early promoter is as shown by the arrow. Ad-MLP (open box) contains adenovirus-2 sequences from coordinates 5779-6231 including the major late promoter, the first exon and part of the intron between the first and second exons of the tripartite leader. TPL (stippled box) contains a synthetic DNA sequence specifying adenovirus-2 sequences 7056-7172, 9634-9693 (containing the acceptor splice site of the second exon of the tripartite leader, the second exon and part of the third exon of the tripartite leader) and a multiple cloning site (MCS) containing sites for KpnI, SmaI, and BglII. pA (hatched box) contains SV40 sequences from 4127-4100 and 2770-2533 that include the polyadenylation and termination signals for early transcription. VA (solid box) contains adenovirus-2 sequences from 10226-11555 that include the virus-associated RNA genes (VAI and VAII), and a NheI site located approximately 570 base pairs downstream from the MCS. The solid lines are derived from pBR322 and represent (starting after the pA sequences and proceeding clockwise) coordinates 29-23, 651-185 (at which point the VA sequences are inserted) 29-1, 4363-2486, and 1094-375. pDC201 is a derivative of pMLSV, previously described by Cosman et al., *Nature* 312:768 (1984).

COS-7 cells are grown and transfected as described by Cosman et al., supra, with the plasmid DNA from a 1.5 ml culture of *E. coli* DH5 α (rec A⁻) transformed with SmaI-cut pDC201 comprising an inserted hIL-7 cDNA (see Example 3, above). In a preferred embodiment, a hIL-7 cDNA spliced to a human IL-2 receptor (p55, Tac antigen) signal sequence is employed to enhance secretion of recombinant hIL-7 from transfected COS-7 cells.

In this embodiment, the pDC201 plasmid having the hIL-7 cDNA insert is cut with ClaI and NheI, and the resulting ClaI-NheI fragment (containing the C-terminal portion of the human IL-7 coding sequence) ligated to the following oligonucleotide, which regenerates the sequence encoding the first 19 amino acids of mature human IL-7 up to and including an internal ClaI site:

```
                    EcoRV
AT TGT GAT ATC GAA GGT AAA GAT GGC AAA CAA TAT GAG ...
TA ACA CTA TAG CTT CCA TTT CTA CCG TTT GTT ATA CTC ...
Asp Cys Asp Ile Glu Gly Lys Asp Gly Lys Gln Tyr Glu ...

ClaI
... AGT GTT CTA ATG GTC AGC AT
... TCA CAA GAT TAC CAG TCG TAGC
... Ser Val Leu Met Val Ser.
```

A PvuII-XbaI fragment of a human IL-2 receptor cDNA is then excised from pMLSV-N1/N4-S [ATCC 39890; see EPA 162,699 and Cosman et al., supra]. This plasmid includes a PvuII site just upstream of the PstI site disclosed in the cited publications. The PvuII-XbaI fragment is isolated and blunted with T4 DNA polymerase and ligated to BamHI linkers. This fragment is then cloned into a BamHI-cut intermediate vector. After cleavage with BamHI, the resulting fragment is isolated and cloned into BglII-cut pDC201 to provide pDC201/IL-2R. To splice the IL-2 receptor leader to mature hIL-7, pDC201/IL-2R is cut with SstI, blunted, and then cut with NheI and the resulting vector fragment ligated to the hIL-7 fragment assembled using the foregoing oligonucleotide. When transfected into COS-7 cells, the resulting vector induces high-level transient expression of hIL-7.

An alternative mammalian cell expression system for human IL-7 is assembled by inserting the foregoing IL-2R/IL-7 construction into a mammalian stable expression vector containing a selectable marker, which is then introduced into baby hamster kidney (BHK) cells. The expression vector is constructed as follows. A SmaI-HincII cDNA fragment is excised from the foregoing pDC201/hIL-2R/hIL-7 plasmid assembled as described above, and cloned into the repaired (Klenow polymerase) BamH1 site of a mammalian expression vector, pNPV1, which comprises an SV40 origin of replication and viral enhancer sequences attached to a mouse metallothionein promoter (MT-1). This hybrid promoter displays a high level of stable, constitutive expression in a variety of mammalian cell types. pNPV1 also contains the normal dihydrofolate reductase (DHFR) DNA sequence which enables methotrexate selection for mammalian cells haboring this plasmid. DHFR sequence amplification events in such cells can be selected by using elevated methotrexate concentrations. In this way, one also generally amplifies the contiguous DNA sequences and thus achieves enhanced expression.

pNPV1 contains, in sequence, (a) an approximately 200 bp segment comprising a truncated MT-1 promoter derived from a KpnI-BamHI fragment of MThGH111 [Palmiter et al., *Science* 222:809 (1983)]; (b) the hIL-7 cDNA fragment described above; (c) an approximately 200 bp fragment including the SV40 termination signal derived from a HindIII-BamHI fragment of pSV2neo [Southern and Berg, *J. Mol. Appl. Genet.* 1:327 (1982)]; (d) bacterial sequences from pUC18 [Norrander et al., *Gene* 26:101 (1983)] enabling replication in *E. coli*; (e) an approximately 850 bp sequence containing the wild-type DHFR (dihydrofolate reductase) coding sequence and SV40 termination signals derived from a CfoI fragment of pSV2-DHFR [Subramani et al., *Mol. Cell Biol.* 1:854 (1981)]; and (f) a 350 bp fragment including SV40 sequences from coordinates 5171-270 including the origin of replication, enhancer sequences and early and late promoters, oriented to promote transcription of the DHFR cDNA and enhance transcription of the hIL-7 cDNA driven by the truncated MT-1 promoter.

Selection and expression were conducted using adherent BHKtk-ts 13 cells (ATCC CRL 1632), described by Waechter, et al., *Proc. Natl. Acad. Sci. USA* 79:1106 (1982), and Talavera, et al., *J. Cell Physiol.* 92:425 (1977). These cells are capable of both high mannose and complex oligosaccharide protein modification. After linearization of the expression plasmid with Sal1, the DNA is introduced into BHK cells by electroporation at 300 volts at 960 microfarads. Suitable electoporation techniques are disclosed by Ausubel et al, eds., supra, at 9.3.1. After 48 hours, 1 micromolar methotrexate was introduced into the culture medium and resistant colonies are selected after a two week period. Representative clones are bioassayed for secretion of hIL-7 into the culture supernatant fraction. The highest expressing clones are then subjected to further selection regimes using 10, 20 and 50 micromolar methotrexate. Resistant colonies are further analyzed to identify high expression level clones. The BHK lines selected using this protocol are adherent cells and scale-up production schemes can be devised involving either suspension growth using beads or growth in bioreactors using hollow fibre technology. BHK cells can be readily adapted to growth as suspension cells.

EXAMPLE 8

Use of IL-7 to Stimulate Proliferation of Immature T-Cells and Thymocytes

To demonstrate that IL-7 stimulates proliferation of various lineages and stages of T cells, thymocytes from fetal and adult mice were cultured in the presence of crude and purified preparations of recombinant murine IL-7.

The thymus, which is responsible for the development and/or differentiation of the cellular immune response, is comprised of a heterogeneous population of T-cells. The vast majority, approximately 80-85% of the cells, are phenotypically unique (CD4+/CD8+) and functionally inept. More mature cells, both functionally and phenotypically, are also present in the thymus. These cells or single positives (CD4+/CD8− or CD4−/CD8+) comprise approximately 5-10% of the thymocytes and are capable of responding to various immunologic stimuli. Also present in the thymus is a population of CD4−/CD8− cells which is thought to be the earliest cell in T-cell ontogeny. Within the CD4−/CD8− subset resides cells capable of repopulating the thymus of immunocompromised recipients and giving rise to the other thymocyte populations.

It is now known that early thymocytes, for example, L3T4−/Lyt2− or CD4−/CD8− cells, can repopulate the thymus of irradiated recipients and differentiate into the various thymocyte subpopulations (i.e., CD4+/CD8−, CD4−/CD8+, and CD4+/CD8+). To determine the effects of IL-7 upon thymocyte proliferation, various thymocyte preparations were incubated in the presence of purified mIL-7 and [$^3$H]-thymidine, and the relative levels of incorporated radioactivity were measured by scintillation counting. In the following series of experiments, culture supernatants containing IL-7 derived from a COS-7 cell line transformed with an expression vector comprising a murine IL-7 cDNA were prepared as described in Example 3. These supernatants were used directly or purified to a single 25 kd protein species as detailed in Example 1. Upon purification, the recombinant mIL-7 had a specific activity of approximately $8 \times 10^5$ units/µg of protein.

In thymocyte proliferation assays, adult C3H/HeJ or C57BL/6J thymocytes were cultured at a density of $10^6$ cells/well in Costar 96 well flat bottom microtiter plates (Cambridge, Mass., USA) in RPMI-1640 medium supplemented with 10% fetal bovine serum, $5 \times 10^{-5}$M 2-mercaptoethanol, 50 µg/ml glutamine in a final volume of 0.2 ml. Recombinant murine IL-2 was added to cultures at a concentration of 50 ng/ml, while rIL-7 was added at a 1:50 dilution of crude COS-7 supernatant containing approximately 1.25 ng/ml mIL-7. $^3$H-thymidine was added to culture wells for the last six hours of a 72 hour culture. Data are expressed in counts per minute (cpm) in Table 2, below, as the arithmetic means of quadruplicate assays.

The mitogenic capabilities of IL-7 were evaluated on the earliest T-cells, or thy+ CD4−/CD8− thymocytes, both alone and in the presence of Con A. Two sources of CD4−/CD8− thymocytes were used. CD4−/CD8− thymocytes were obtained from adult thymuses by negative selection using antibody and complement-mediated cytolysis. C57BL/6J adult thymocytes were incubated at 4° C. for 45 minutes with equal volumes of anti-L3T4 and anti-Lyt2 mAb. Following this incubaton the cells were centrifuged, the supernatant aspirated and the cells resuspended in the culture supernatant of the Mar 18.5 cell line (anti-rat kappa chain mAb) (American Type Tissue Center, Rockville, md., USA) (1 ml/$10^7$ cells) for 30 minutes at 4° C. After centrifugation, the cells were resuspended in a 1:10 dilution of rabbit complement and incubated for 30 minutes at 37° C. The cells were then washed once and the viable cells isolated by centrifugation through a discontinuous density gradient. The resultant cells were approximately 0.1% of the starting number. They were more than 98% viable and analysis of CD4 and CD8 expression by immunofluorescent staining and flow cytometry showed them to be less than 4% CD4+ or CD8+.

CD4−/CD8− thymocytes were also obtained as Day 13 fetal thymocytes which consists predominantly (>99%) of CD4−/CD8− Thy1+ cells. Day 13 fetal thymocytes (Day 0 being the first day of vaginal plug) were cultured at a density of $5 \times 10^4$ cells/well in round bottom plates according to the method of Raulet, *Nature* 314:101 (1985). When these cells were cultured with recombinant IL-7, a proliferative response was observed as shown in Table 2. CD4−/CD8− thymocytes can proliferate in response to IL-7 in the absence of any comitogen.

The addition of the plant lectin concanavalin A (Con A, 2.5 μg/ml) to the cultures markedly augmented to response of CD4−/CD8− thymocytes to IL-2 and IL-7. Adult CD4−/CD8− responded quite vigorously to Con A alone, while the addition of IL-2 to the cultures gave a three-fold enhancement in proliferation. The addition of IL-7 more than doubled the proliferative response of these cells. Fetal thymocytes did not measurably respond to Con A alone, but in the presence of IL-2 or IL-7 significant proliferation was observed. These data demonstrate that cells of the least mature intrathymic stage of T-cell differentiation can be stimulated to proliferate by IL-7, indicating the role of this cytokine in T-cell differentiation and maturation.

TABLE 2

IL-7-Driven Proliferation of Adult and Fetal Thymocytes
(Mean cpm/culture well × $10^{-3}$ in thymocyte proliferation assay)

| Thymocytes | Con A | Culture Additions | | |
|---|---|---|---|---|
| | | None | IL-2 | IL-7 |
| Adult CD4−/CD8− | − | 0.7 | 19.1 | 11.7 |
| | + | 43.3 | 130.3 | 98.4 |
| Day 13 Fetal | − | 0.6 | 11.5 | 6.7 |
| | + | 1.0 | 23.3 | 12.9 |

The relative efficiency of IL-7 as a T-cell mitogen was also investigated, both by itself and in the presence of a co-mitogenic stimulus, PHA, and compared to two other T-cell growth factors, Interleukin-2 (IL-2) and Interleukin-4 (IL-4). Both IL-2 and IL-7 directly stimulated thymocyte proliferation; however, IL-2 was approximately ten-fold more active on a weight basis than IL-7. Even at concentrations as high as 1 μg/ml, IL-4 was a poor mitogen for thymocyte cultures. However, when the lectin phytohemaglutinin (PHA) was added to the cultures at a final concentration of 1% (vol/vol) a profound increase in IL-2-, IL-4-, and IL-7-dependent proliferation was seen.

IL-7 acts independently of IL-2, IL-4 or PHA in stimulating thymocyte proliferation. For example, at IL-2 concentrations which were saturating for thymocyte proliferation (1-1000 ng per ml), IL-7 (at approximately 1-2 ng per ml) significantly enhanced the proliferative response, resulting in approximately a 50% increase in tritiated thymidine incorporation. In a similar fashion, an increase in IL-4-dependent proliferation was also seen in the presence of IL-7. Furthermore, IL-7-driven proliferation of thymocytes was not inhibited by anti-IL-2 receptor monoclonal antibody at concentrations capable of inhibiting IL-2-driven thymocyte proliferation. An anti-mIL-4 monoclonal also did not inhibit the ability of IL-7 to induce thymocyte proliferation.

The foregoing experiments indicate that IL-7 is capable of stimulating the proliferation of immature T cells and is also a potent co-stimulator of mature T cells in the presence of a mitogen.

EXAMPLE 9

Administration of IL-7 to Normal Mice

A series of experiments were conducted to determine the effects of intraperitoneal administration of mIL-7 in normal C57BL/6J mice (Jackson Laboratory, Bar Harbor, Me., USA). Murine IL-7, prepared by COS-7 cell expression as described in Example 3, was administered on days 0 through 4. Cellularity, function and cell surface antigen phenotype in the spleen, peritoneal cavity, peripheral blood, thymus and bone marrow were examined on days 5 and 8, at dosages of 40 ng, 200 ng, and 1 μg per animal, using five mice per dosage group.

Bone marrow granulocyte/macrophage colony forming units (CFU-GM) were elevated on day 8 in mice receiving all doses of IL-7, with the 40 ng group showing the maximum increase compared to control mice receiving excipient only. In like fashion, IL-7-responsive marrow cells were increased in the same mice, with the maximum effect occurring in the 40 ng group. Bone marrow megakaryocyte CFU (CFU-MK) were increased in all dose groups and were maximal (3× over controls) on day 8 in mice receiving 200 ng. In the spleen, CFU-GM were increased only in mice receiving the highest dose of IL-7.

Peripheral blood cellularity increased 1.5 to 2.5× on day 5 in all dose groups, and remained at approximately 2.5× in the high dose group on day 8. Similar kinetics were observed for peritoneal cavity cellularity, but increases here were up to 3.5×. Bone marrow increased ~1.5× on day 5 but was not different from controls on day 8. In spleen, 1.5-1.8× increases in cellularity were seen on days 5 and 8 in the high dose group. Thymus cellularity was unaltered on day 5 but increased 2× on day 8 in the high dose group.

EXAMPLE 10

Preparation of Antibodies Immunoreactive with IL-7

Preparations of purified native or recombinant IL-7, for example, human IL-7, are employed to generate polyclonal antisera or preferably, monoclonal antibodies against IL-7 using conventional techniques, for example, those disclosed in U.S. Pat. No. 4,411,993. Such antibodies are likely to be useful in detecting IL-7, or in neutralizing IL-7 biological activity in assays or experiments involving multiple lymphokines.

To immunize mice, a substantially pure IL-7 preparation is emulsified in complete Freund's adjuvant and injected in amounts ranging from 10-100 μg subcutaneously into Balb/c mice. Ten to twelve days later, the immunized animals are boosted with additional IL-7 emulsified in incomplete Freund's adjuvant and periodically boosted thereafter on a weekly to biweekly immunization schedule. Serum samples are periodically taken by retro-orbital bleeding or tail-tip excision for testing by dot-blot assay (antibody sandwich) or ELISA (enzyme-linked immunosorbent assay). Other assay procedures are also suitable. Following detection of an appropriate antibody titer, positive animals are given an intravenous injection of antigen in saline. Three to four days later, the animals are sacrificed, splenocytes harvested, and fused to the murine myeloma cell line NS1. Hybridoma cell lines generated by this procedure are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated can be screened by ELISA for reactivity with IL-7, for example, by adaptations of the techniques disclosed by Engvall et al., *Immunochemistry* 8:871 (1971) and in U.S. Pat. No. 4,703,004. Positive clones are then injected into the peritoneal cavities of syngeneic Balb/c mice to produce ascites containing high concentrations (>1 mg/ml) of anti-IL-7 monoclonal antibody. The resulting monoclonal antibody can be purified by ammonium sulfate precipitation followed by gel exclusion chromatography, and/or affinity chromatography based on binding of antibody to Protein A of *Staphylococcus aureus*.

We claim:

1. Essentially homogeneous purified interleukin-7 (IL-7) wherein the purified IL-7 displays the ability to induce proliferation of bone marrow-derived pre-B cells; wherein a native glycosylated full length mature form of said IL-7 has a molecular weight of about 25,000 daltons as determined by SDS-PAGE; wherein the N-terminus of the mature form of the IL-7 protein comprises an amino acid sequence selected from Asp-Cys-Asp-Ile-Glu-Gly-Lys-Asp- and Glu-Cys-His-Ile-Lys-Asp-Lys-Glu.

2. Purified IL-7 according to claim 1, wherein said IL-7 is selected from the group consisting of human IL-7 comprising the amino acid sequence of residues 1-152 of FIG. 5, and murine IL-7 comprising the amino acid sequence of residues 1-129 of FIG. 3.

3. Essentially homogeneous purified human IL-7 having the ability to induce proliferation of bone marrow-derived per-B cells, wherein said IL-7 comprises the amino acid sequence of residues 1-152 in FIG. 5.

4. A pharmaceutical composition comprising an effective amount of an essentially homogeneous purified human IL-7 in admixture with a suitable diluent or carrier, wherein said purified human IL-7 induces proliferation of bone marrow-derived pre-B cells; wherein a native glycosylated full length mature form of said IL-7 has a molecular weight of about 25,000 daltons as determined by SDS-PAGE; wherein the N-terminus of the mature form of the IL-7 protein comprises the amino acid sequence Asp-Cys-Asp-Ile-Glu-Gly-Lys-Asp-.

* * * * *